(12) United States Patent
Parekh et al.

(10) Patent No.: US 11,566,044 B2
(45) Date of Patent: Jan. 31, 2023

(54) DISULFIDE BOND CONTAINING COMPOUNDS AND USES THEREOF

(71) Applicant: THE UNIVERSITY OF QUEENSLAND, St. Lucia (AU)

(72) Inventors: Harendra Parekh, Woolloongabba (AU); Karnaker Reddy Tupally, Woolloongabba (AU)

(73) Assignee: THE UNIVERSITY OF QUEENSLAND, Queensland (AU)

( * ) Notice: Subject to any disclaimer, the term of this patent is extended or adjusted under 35 U.S.C. 154(b) by 0 days.

(21) Appl. No.: 16/633,801

(22) PCT Filed: Jul. 26, 2018

(86) PCT No.: PCT/AU2018/050773
§ 371 (c)(1),
(2) Date: Jan. 24, 2020

(87) PCT Pub. No.: WO2019/018892
PCT Pub. Date: Jan. 31, 2019

(65) Prior Publication Data
US 2020/0207810 A1    Jul. 2, 2020

(30) Foreign Application Priority Data
Jul. 26, 2017    (AU) ................ 2017902927

(51) Int. Cl.
*C07K 7/06*       (2006.01)
*C07K 5/11*       (2006.01)
(Continued)

(52) U.S. Cl.
CPC .............. *C07K 5/0215* (2013.01); *C07K 5/06* (2013.01); *C07K 5/1019* (2013.01); *C07K 7/06* (2013.01)

(58) Field of Classification Search
CPC . C07C 2603/18; C07C 323/59; C07K 5/0215; C07K 5/08; C07K 5/081;
(Continued)

(56) References Cited

U.S. PATENT DOCUMENTS 5,411,991 A * 5/1995 Shander .................... A61Q 7/02
                                                                514/665
5,776,962 A    7/1998 Gross et al.
(Continued)

FOREIGN PATENT DOCUMENTS

EP          163550       12/1985
GB         1556455       11/1979
(Continued)

OTHER PUBLICATIONS

Greene's Protective Groups in Organic Synthesis (Greene et al., Greene's Protective Groups in Organic Synthesis, 5th Ed, John Wiley & Sons, Inc., 2007, ISBN-10: 0-471-69754-0, attached as pdf, pp. v-vii, 1-5 (Year: 2007).*

(Continued)

*Primary Examiner* — Randall L Beane
(74) *Attorney, Agent, or Firm* — Nixon & Vanderhye P.C.

(57) ABSTRACT

There is provided a range of novel disulfide bond containing compounds. These disulfide bond containing compounds can be used in a variety of applications such as solid phase peptide synthesis, solid phase organic synthesis, formation of dendrimers, formation of macromolecules and formation cyclic peptides; and as a component of a delivery vehicle with a bioactive molecule.

11 Claims, 14 Drawing Sheets

(51) Int. Cl.
  *C07K 5/02* (2006.01)
  *C07K 5/06* (2006.01)
(58) Field of Classification Search
  CPC ...... C07K 5/1013; C07K 5/1019; C07K 7/02; C07K 7/06
  See application file for complete search history.

(56) References Cited

U.S. PATENT DOCUMENTS

| | | | |
|---|---|---|---|
| 2004/0248871 | A1 | 12/2004 | Farjanel et al. |
| 2017/0112891 | A1 | 4/2017 | Dragovich et al. |
| 2017/0342046 | A1* | 11/2017 | Vu .................. C07D 261/18 |

FOREIGN PATENT DOCUMENTS

| | | |
|---|---|---|
| JP | 04120076 | 4/1992 |
| JP | 2877475 | 3/1999 |
| JP | 11327103 | 11/1999 |
| WO | WO 2002/096910 | 12/2002 |
| WO | 2012/128868 | 9/2012 |
| WO | 2016/036794 | 3/2016 |
| WO | WO 2016/086103 | 6/2016 |
| WO | 2016/111751 | 7/2016 |
| WO | 2017/003940 | 1/2017 |

OTHER PUBLICATIONS

CAS registry No. 1401283-79-1 (published Oct. 17, 2012).
Brulisauer et al., Disulfide-containing parenteral delivery systems and their redox-biological fate, Journal of Controlled Release, 2014, 195, pp. 147-154.
Chen, L. et al, "Chemical Syntheses and Biological Studies on Dimeric Chimeras of Oxytocin and the V2-Antagonist, d(CH2)5[D-Ile2,Ile4]arginine Vasopressin", J Med Chem 1999, 42(24), pp. 5002-5009.
Field L. and Giles P.M., Jr., "Biologically Oriented Organic Sulfur Chemistry. VI. Uses of o-Carboxyphenyl o-Carboxybenzenethiolsulfonate with Thiols", Journal of Organic Chemistry 1971, 36, pp. 309-313.
Field L. et al., "Biologically Oriented Organic Sulfur Chemistry. 8. Structure-Activity Relationships of Penicillamine Analogs and Derivatives", Journal of Medicinal Chemistry 1971, 14, pp. 868-872.
Field L. et al., "Organic Disulfides and Related Substances. VIII. Preparation and Oxidation of Some Unsymmetrical Dialkyl and Alkyl Pyridinium Disulfides", Journal of Organic Chemistry 1964, 29, pp. 1632-1635.
Field L. and Ravichandran R., "Organic Disulfides and Related Substances. 42. Synthesis and Properties of Some Tertiary Disulfides, Especially Involving Penicillamine", Journal of Organic Chemistry 1979, 44, pp. 2624-2629.
Flouret G. et al, "Antagonists of Oxytocin Featuring Replacement with Modified β-Mercaptopropionic Acids at Position 1", J Peptide Science 2002, 8(7), pp. 314-326.
Flouret G. et al, Design of Potent Oxytocin Antagonists Featuring D-Tryptophan at Position 2:, J Med Chem 1991, 34(2), pp. 642-646.
Grandjean, C. et al., "Convergent synthesis of D-(-)-quinic and shikimic acid-containing denrimers as potential C-lectin ligands by sulfide ligation of unprotected fragments", J. Chem. Soc. Perkin Trans., Jan. 1999, vol. 20, pp. 2967-2975.
Halverson, P.B. et al., "Toxicity of penicillamine", JAMA 1978, 240, pp. 1870-1871.
Hunter, R. et al., "Inexpensive, One-Pot Synthesis of Unsymmetrical Disulfides Using 1-Chlorobenzotriazole," J. Org. Chem. 2006, 71, pp. 8268-8271.
Hunter, R. et al., "Efficient One-Pot Synthesis of Unsymmetrical Cysteine Disulfides," SYNLETT 2008, No. 2, pp. 0252-0254.
Stellenboom N. et al., "One-Pot Synthesis of Unsymmetrical Disulfides using 1-chlorobenzotriazole as oxidant: Interception of the sulfenyl chloride intermediate," Tetrahedron 66 (2010), pp. 3228-3241.
Ichimupgs. ra A. et al., "Reactivity of Coordinated Disulfides. 1. Nucleophilic Cleavage of the Sulfur-Sulfur Bond", Journal of the American Chemical Society 1983, 105, pp. 844-850.
Kellogg B. A., et al., "Disulfide-Linked Antibody-Maytansinoid Conjugates: Optimization of In Vivo Activity by Varying the Steric Hindrance at Carbon Atoms Adjacent to the Disulfide Linkage", Bioconjugate Chemistry, 2011, 22, pp. 717-727.
LiverTox—Clinical and Research Information on Drug-Induced Liver Injury—US National Library of Medicine. Drug Record: Pinicillamine. Downloaded Jun. 15, 2018; pp. 1-8.
Luo K. et al., "Arginine functionalized peptide dendrimers as potential gene delivery vehicles", Biomaterials, 33: pp. 4917-4927 (2012).
Luo K. et al., "Peptide dendrimers as efficient and biocompatible gene delivery vectors: synthesis and in vitro characterization", Journal of controlled release, 155: pp. 77-87 (2011).
Mery J. et al. "Disulfide linkage to polyacrylic resin for automated Fmoc peptide synthesis. Immunochemical applications of peptide resins and mercaptoamide peptides," Int. J Peptide & Protein Research 1993, 42(1), pp. 44-52.
Mueller C. E. et al., Lipophilic disulfide prodrugs—syntheses and disulfide bond cleavage, International Journal of Pharmaceutics 1989, 57, pp. 41-47.
Mutalik S. et al., Enhancement in deposition and permeation of 5-fluorouracil through human epidermis assisted by peptide dendrimers' Drug Delivery, 21(1): pp. 44-54 (2014).
Mutalik S. et al., "Iontophoresis-mediated transdermal permeation of peptide dendrimers across human epidermis", Skin Pharmacol Physiol, (2013), 26, pp. 127-138.
Ouyang, D. et al., Reducible Disulfide-Based Non-Viral Gene Delivery Systems' Mini-Reviews in Medicinal Chemistry, Sep. 2009, pp. 1242-1250.
Pallin, T.D. and Tam J.P., "Assembly of cyclic peptide dendrimers from unprotected linear building blocks in aqueous solution", Chem. Commun., 1996, vol. 11, pp. 1345-1346.
Phillips D.J. and Gibson M.I. "Redox-Sensitive Materials for Drug Delivery: Targeting the Correct Intracellular Environment, Tuning Release Rates, and Appropriate Predictive Systems" Antioxidants & Redox Signaling, 21(5):786 (2014).
Schafer, F.Q. and G.R. Buettner, "Redox environment of the cell as viewed through the redox state of the glutathione disulfide/glutathione couple," Free Radical Biology and Medicine, 2001, 30(11): pp. 1191-1212.
Senter, P.D., 'Potent antibody drug conjugates for cancer therapy', Current Opinion in Chemical Biology 2009, 13, pp. 235-244.
Shah, N.D., et al., "Asymmetric peptide dendrimers are effective linkers for antibody-mediated delivery of diverse payloads to B cells in vitro and in vivo", Pharmaceutical research, 2014. 31(11): pp. 3150-3160.
Shah N. et al., Low-generation asymmetric dendrimers exhibit minimal toxicity and effectively complex DNA, Journal of Peptide Science, 2011, 17, pp. 470-478.
Sisley M.J. et al., "Reaction of thiols with N-bonded sulfenamide complexes of cobalt(III): steric effect and reaction pathway", Inorganic Chemistry 2005, 44, pp. 293-299.
Tegge, W. et al., "Synthesis of cyclic peptides and peptide libraries on a new disulfide linker", J. Pept. Sci. 2007, 13: pp. 693-699.
Threadgill, M.D. and Gledhill, A.P., "Synthesis of peptides containing S-(N-alkylcarbamoyl) cysteine residues, metabolites of N-alkylformamides in rodents and in humans", J. Org. Chem., 1989, vol. 54, pp. 2940-2949.
Van Rensburg et al, "Reactions of unsymmetrical disulfides. I. Sulfitolysis of sulfur derviatives of cysteamine and cysteine", Archives of Biochemistry and biophysics 1967, 118, pp. 531-535.
Wadhwa S. and Mumper R.J., "Polypeptide conjugates of d-pencillamine and idarubin for anticancer therapy", Journal of Controlled Release 2012, 158, pp. 215-223.
Walshe, J.M., "Penicllamine neurotoxicity: an hypothesis", International Scholarly Research Network ISRN Neurology, 2011, Article ID 464572.
Weiss R.E. et al., Influence of penicillamine and various analogs on matrix-induced bone formation in rats, Biochemical Medicine 1984, 32, pp. 331-336.

(56) References Cited

OTHER PUBLICATIONS

Wu, C. et al., "Broad Control of Disulfide Stability through Microenvironmental Effects and Analysis in Complex Redox Environments", Biomacromolecules, 2013, 14, pp. 2383-2388.
Defang Ouyang PhD Thesis, Submitted to University of Queensland, Aug. 2010.
Varghese A.J., "Properties of photoaddition products of thymine and cysteine", Biochemistry, Dec. 1973, 2725.
Varghese A.J. "Photochemical addition of glutathione to uracil and thymine" Photochemistry and photobiology 1974, 20, pp. 339-343.
International Search Report for PCT/AU2018/050773 dated Oct. 5, 2018, 6 pages.
Written Opinion of the ISA for PCT/AU2018/050773 dated Oct. 5, 2018, 8 pages.
Chen et al. A Universal GSH-Responsive Nanoplatform for the Delivery of DNA mRNA and Cas9/sgRNA Ribonucleoprotein, ACS Applied Materials and Interfaces, May 25, 2018, 10, 22, pp. 18515-18523.
Kokil, G.R. et al. "Self-Assembling asymmetric peptide-dendrimer micelles—a platform for effective and versatile in vitro nucleic acid delivery", Scientific Reports, Mar. 19, 2018, 8, 4832, pp. 1-16.
Lei, E.K. and Kelley, S.O., 'Delivery and release of small-molecule probes in mitochondria using traceless linkers', Journal of the American Chemical Society, Jun. 30, 2017, vol. 139, p. 9455-9458.
Tupally, K.R. et al. Engineering of a novel, sterically hindered disulphide bridged amino acid: a new generation of bioreducible peptides and drug/gene carrier systems with enhanced biostability, 5th FIP Pharmaceutical Sciences World Congress (PSWC) Melbourne Apr. 13-16, 2014 (Abstract).
Tupally, K.R. et al. Broadening the horizons of bioreducible polymers: Significance and strategies towards the design of disulphide-linked vectors in biological systems, International Conference on BioNano Innovation (ICBNI) Brisbane Jul. 6-10, 2014 (Poster).
Tupally, K.R. et al., Development and evaluation of biochemically stable disulfide-bridged amino acids: a novel, facile approach for site-specific and sequential introduction of disulfide bridges into biomolecules, American Peptide Symposium (APS), Orlando Florida, USA Jun. 20-25, 2015 (Poster).
Tupally, K.R. et al. Development and evaluation of sterically stable disulfide-bridged amino acids: a novel, facile approach for site-specific and sequential introduction of disulfide bridges during solid phase peptide synthesis (SPPS), Boulder Peptide Symposium, Boulder Colorado, USA Sep. 28-Oct. 1, 2015 (Poster).
Tupally, K.R. et al. Synthesis of bioreducible peptide-based carriers: a novel approach for site-specific and sequential introduction of disulfide bridges during SPPS, Brisbane Biological and Organic Chemistry Symposium (BBOCS), Royal Australian Chemical Institute, Brisbane, Australia, Dec. 2014 (Poster).
Tupally, K.R. et al. Synthesis and Application of Novel Disulfide Containing Amino Acid for Drug/Gene Delivery and Therapeutic Peptides, Brisbane Biological and Organic Chemistry Symposium (BBOCS), Royal Australian Chemical Institute, Brisbane, Australia, Dec. 2013 (Poster).
Tupally, K.R. et al. Application of bioresponsive building blocks towards the facile synthesis of bioreducible branched and linear peptides, Boulder Peptide Symposium, Boulder Colorado, USA, Sep. 25-28, 2017 (Poster).

* cited by examiner

DISULFIDE BOND CONTAINING COMPOUNDS AND USES THEREOF

This application is the U.S. national phase of International Application No. PCT/AU2018/050773 filed Jul. 26, 2018 which designated the U.S. and claims priority to AU Patent Application No. 2017902927 filed Jul. 26, 2017, the entire contents of each of which are hereby incorporated by reference.

FIELD OF THE INVENTION

The invention relates to disulfide bond containing compounds. More particularly, this invention relates to disulfide bond containing compounds for use in a variety of applications including solid phase peptide synthesis, formation of dendrimers and cyclic peptides and as a component of a delivery vehicle with a bioactive molecule.

BACKGROUND TO THE INVENTION

Any reference to background art herein is not to be construed as an admission that such art constitutes common general knowledge in Australia or elsewhere.

Disulfide (—S—S—) bridges formed between cysteine-based thiols and present within molecules sourced naturally or prepared through chemical means, play a fundamental role in maintaining conformational stability. Marketed peptide drugs comprising site-specific —S—S-bonds are first-hand evidence of this, showing enhanced selectivity, stability and pharmacological activity. However, introduction of —S—S-bridges to a peptide/biomolecule during chemical synthesis remains a significant challenge, largely due to the complex thiol-protection & deprotection strategies needed, base lability of —S—S-bridges, and the inevitable formation of regioisomeric by-products when introduced post-synthetically.

Disulfide bridges are also highly attractive from a drug delivery standpoint, with the potentiation of reduction-triggered release of therapeutics from drug delivery systems driven by vast differences (1000-fold) in glutathione (GSH) levels present intracellularly, versus extracellularly.

This interest has led to the design of disulfide bond containing compounds which can be employed in solid phase peptide synthesis (SPPS) and/or solid phase organic synthesis (SPOS) as well as in drug delivery applications.

Significant challenges remain, however, and most current methods of introducing disulfide bridges into peptides/proteins still do so by forming the —S—S— bond itself from two cysteine residues under oxidising conditions using relatively expensive cross-linking reagents. Further, working with peptides that contain multiple cysteine residues results in a low yield of the desired disulfide bridged-product due to the generation of multiple end-products and purification of a desired target product is problematic, as the heterogeneous mixture of end-products tend to possess very similar physiochemical properties resulting in co-elution during purification.

It would be useful to have an alternative approach which minimises or eliminates the need for such cross-linking reagents as SPDP (succinimidyl 3-(2-pyridyldithio)propionate) and SMCC (succinimidyl 4-(N-maleimidomethyl)cyclohexane-1-carboxylate) and which minimises the formation of multiple disulfide bond containing side products. A more directed approach to the introduction of disulfide bonds into peptide structures would be highly advantageous.

SUMMARY OF THE INVENTION

It has been found that certain building blocks comprising a disulfide bond and carboxylic acid and/or amino functionalities can be used as pre-synthesised 'disulfide bond containing' amino acids which can be used in SPPS/SPOS and incorporated into various peptides and dendrimers and other delivery vehicles for therapeutics.

Particularly, it has been found that such disulfide bond containing amino acid-like compounds can be preferentially stabilised by the inclusion of moieties adjacent the disulfide bond which provide suitable steric and electronic effects. This stabilises the disulfide bond to basic conditions typically encountered during SPPS/SPOS and/or to weak reducing conditions, such as are found in the human body extracellularly, but still allows reduction of the bond under glutathione concentrations typically found intracellularly thereby providing for controlled disulfide bond reduction and, so, the potential for selective drug release or peptide degradation.

The present invention identifies particularly desirable structural characteristics for such disulfide bond containing compounds and details a number of their applications.

A first aspect of the invention provides for a compound of formula I, or a salt thereof:

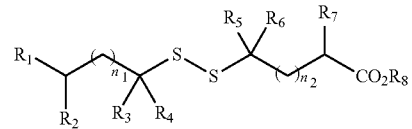

Formula I wherein, $R_1$ is selected from the group consisting of hydrogen, $R_9R_9'N$— and —$CO_2R_{10}$;

$R_2$ is selected from the group consisting of hydrogen and methyl;

$R_3$, $R_4$, $R_5$ and $R_6$ are independently selected from the group consisting of hydrogen and $C_1$ to $C_4$ alkyl, or, $R_3$ and $R_4$, when taken together along with the carbon to which they are bound and/or $R_5$ and $R_6$, when taken together along with the carbon to which they are bound form a cyclic structure selected from the group consisting of $C_3$ to $C_5$ cycloalkyl and $C_3$ to $C_5$ oxygen-containing, nitrogen-containing or sulphur-containing heterocycle, each of which may be substituted or unsubstituted;

$R_7$ is selected from the group consisting of hydrogen and $R_9R_9'N$—;

$R_8$ is selected from the group consisting of hydrogen, a counterion, and a substituted or unsubstituted carboxylic acid protecting group;

$R_9$ and $R_9'$ are independently selected from the group consisting of hydrogen, substituted or unsubstituted $C_1$ to $C_6$ alkyl and a substituted or unsubstituted amine protecting group, or $R_9$ and $R_9'$ together form a substituted or unsubstituted amine protecting group;

$R_{10}$ is selected from the group consisting of hydrogen, a counterion and a substituted or unsubstituted carboxylic acid protecting group;

$n_1$ and $n_2$ are independently 0, 1, 2, 3, or 4; and with the provisos that, at least one of $R_3$, $R_4$, $R_5$ and $R_6$ is not hydrogen;

$R_1$ is not $NH_2$, BocHN or AcHN when all of the following are true: $R_2$ is hydrogen, $R_8$ is hydrogen or methyl, $n_1$ and $n_2$ are 0, $R_7$ is $R_9HN-$, $R_9$ is hydrogen or acetyl, $R_3$ and $R_4$ are hydrogen and $R_5$ and $R_6$ are methyl; and $R_8$ is not phenylisopropyl when all of the following are true: $n_1$ and $n_2$ are 0, $R_1$ is $-CO_2R_{10}$, $R_2$ is hydrogen, $R_3$ and $R_4$ are methyl, $R_5$ and $R_6$ are hydrogen, $R_7$ is $R_9HN-$, $R_9$ is Fmoc, and $R_{10}$ is hydrogen.

In embodiments, the compound is a compound of formula II, or a salt thereof:

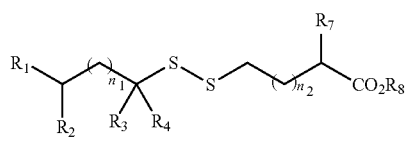

Formula II wherein, $R_1$, $R_2$, $R_3$, $R_4$, $R_7$, $R_8$, $R_9$, $R_9'$, $R_{10}$ and $n_1$ and $n_2$ are as defined previously and wherein, when $n_1$ and $n_2$ are 0, $R_1$ is $-CO_2R_{10}$, $R_2$ is hydrogen, $R_3$ and $R_4$ are methyl, $R_7$ is $R_9HN-$, $R_9$ is Fmoc, and $R_{10}$ is hydrogen, then $R_8$ is not phenylisopropyl.

In certain embodiments, the compound is a compound of formula III, or a salt thereof:

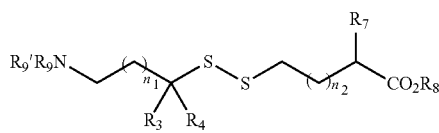

Formula III wherein, $R_3$, $R_4$, $R_7$, $R_8$, $R_9$, $R_9'$, and $n_1$ and $n_2$ are as defined previously.

In embodiments, the compound is a compound of formula IV, or a salt thereof:

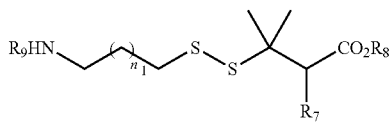

Formula IV wherein $R_7$, $R_8$, $R_9$, $R_9'$ and $n_1$ are as defined for formula I and wherein when $n_1$ is 0, $R_7$ is $NH_2$ or NHAc, and $R_8$ is hydrogen or methyl, then $R_9$ is not hydrogen, Boc, or acetyl.

In embodiments, the compound, or salt thereof, is selected from the group consisting of:

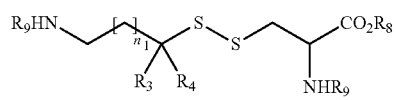

Formula V

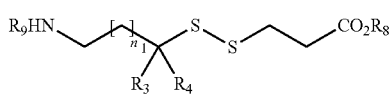

Formula VI

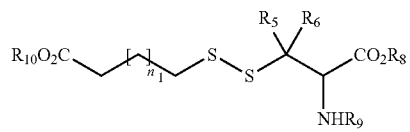

Formula VII

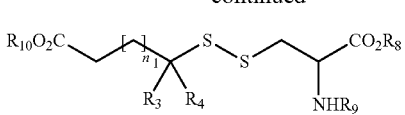

Formula VIII

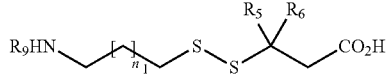

Formula IX

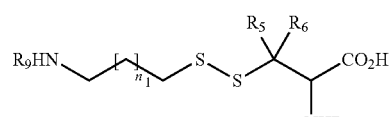

Formula X wherein, $R_3$, $R_4$, $R_5$, $R_6$, $R_8$, $R_9$, $R_{10}$ and $n_1$, as appropriate for each of formula V to X, are as defined previously.

In an embodiment, the compound, or salt thereof, is a compound of formula XI:

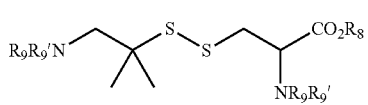

Formula XI wherein $R_8$, $R_9$ and $R_9'$ are as defined previously.

In other words, the compound, or salt thereof, is a compound of formula XI:

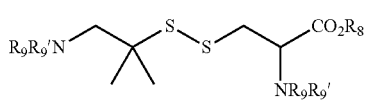

Formula XI wherein $R_8$ is selected from the group consisting of hydrogen, a counterion and a substituted or unsubstituted carboxylic acid protecting group; and $R_9$ and $R_9'$ are independently selected from the group consisting of hydrogen, substituted or unsubstituted $C_1$ to $C_6$ alkyl and a substituted or unsubstituted amine protecting group, or $R_9$ and $R_9'$ together form a substituted or unsubstituted amine protecting group.

In embodiments, the compound, or salt thereof, is a compound of formula XII:

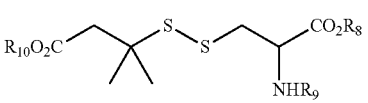

Formula XII wherein $R_8$ is selected from the group consisting of hydrogen, a counterion and a substituted or unsubstituted carboxylic acid protecting group;

$R_9$ is selected from the group consisting of hydrogen, substituted or unsubstituted $C_1$ to $C_6$ alkyl and a substituted or unsubstituted amine protecting group; and $R_{10}$ is selected from the group consisting of hydrogen, a counterion and a substituted or unsubstituted carboxylic acid protecting group.

In embodiments, the compound, or salt thereof, is a compound of formula XIII:

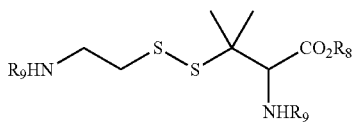

Formula XIII wherein $R_8$ is selected from the group consisting of hydrogen, a counterion and a substituted or unsubstituted carboxylic acid protecting group; and each $R_9$ is independently selected from the group consisting of hydrogen, substituted or unsubstituted $C_1$ to $C_6$ alkyl and a substituted or unsubstituted amine protecting group.

In embodiments, the compound, or salt thereof, is a compound of formula XIV:

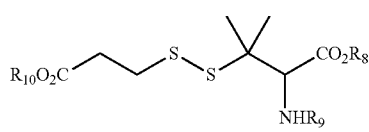

Formula XIV wherein $R_8$ is selected from the group consisting of hydrogen, a counterion and a substituted or unsubstituted carboxylic acid protecting group;

$R_9$ is selected from the group consisting of hydrogen, substituted or unsubstituted $C_1$ to $C_6$ alkyl and a substituted or unsubstituted amine protecting group; and $R_{10}$ is selected from the group consisting of hydrogen, a counterion and a substituted or unsubstituted carboxylic acid protecting group.

In embodiments, the compound of Formula I to XIV is lipidated.

A second aspect resides in a method of forming a peptide structure comprising the step of reacting a compound of the first aspect with a complimentary amino acid or bioactive molecule.

A third aspect resides in a peptide structure comprising a compound of the first aspect.

In embodiments, the peptide structure is a linear peptide, cyclic peptide or dendrimeric structure.

In embodiments, the dendrimeric structure is

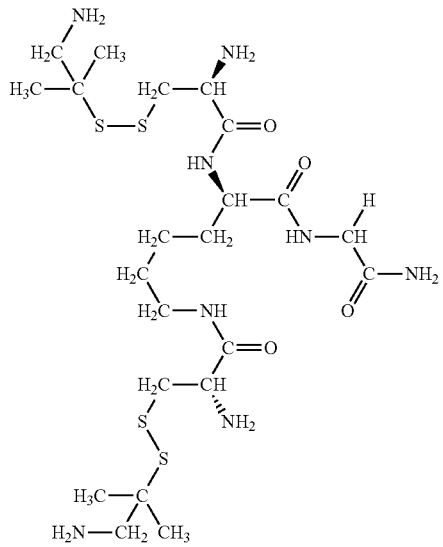

(BD1)

or a salt thereof.

In embodiments, the dendrimeric structure is

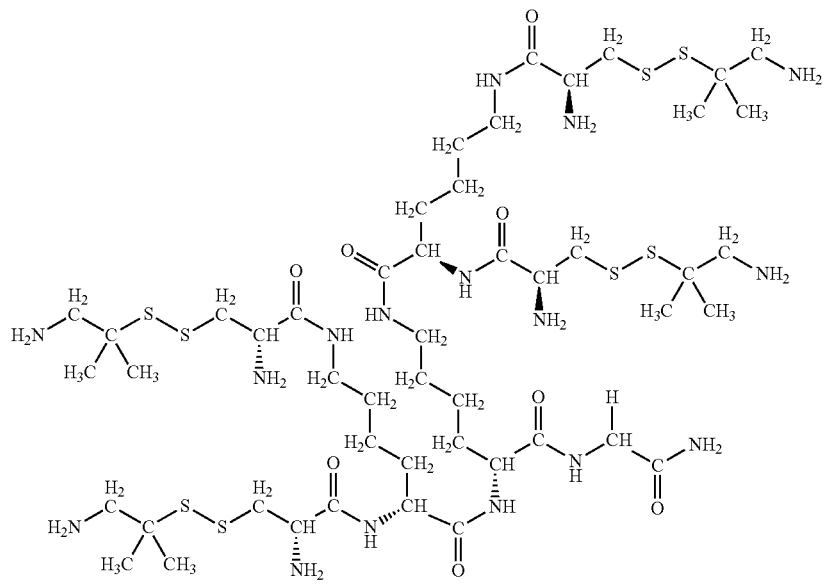

(BD2)

or a salt thereof.

In embodiments, the dendrimeric structure is

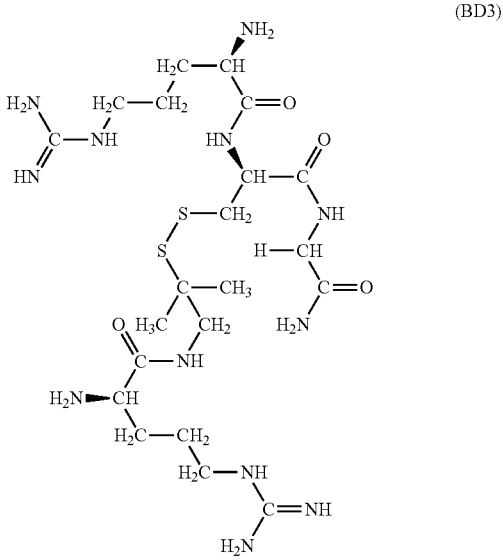 [SMILES: CC(C)(CNC(=O)[C@H](N)CCCNC(=N)N)SSC[C@@H](NC(=O)[C@H](N)CCCNC(=N)N)C(=O)NCC(N)=O]
(BD3)

or a salt thereof.

In embodiments, the dendrimeric structure is

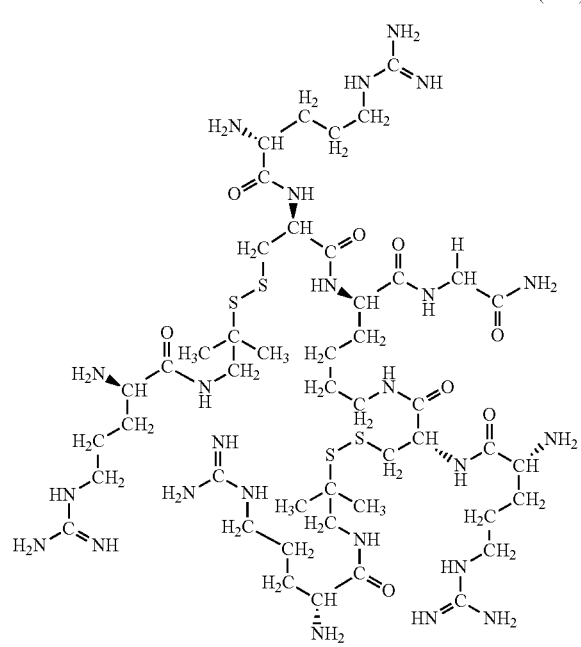
(BD4)

or a salt thereof.

A fourth aspect resides in a delivery vehicle comprising a macromolecule, the macromolecule comprising a compound of the first aspect, wherein the macromolecule is complexed with or bonded to a bioactive molecule.

In embodiments, the macromolecule further comprises a lipid.

In embodiments, the lipidated macromolecule forms liposomes, micelles, solid lipid particles, or any combination thereof.

A fifth aspect resides in a method of delivering a bioactive molecule to a target site in a mammal including the step of providing the delivery vehicle of the fourth aspect to the mammal to thereby deliver the bioactive molecule.

A sixth aspect resides in a tag or probe construct comprising a compound of the first aspect bonded to a tag or probe.

A seventh aspect resides in a pharmaceutical composition for the treatment or prophylaxis of a disease, disorder or condition comprising an effective amount of a peptide structure of the third aspect or delivery vehicle of the fourth aspect and a pharmaceutically acceptable carrier, diluent and/or excipient.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

DETAILED DESCRIPTION

Figure 1:
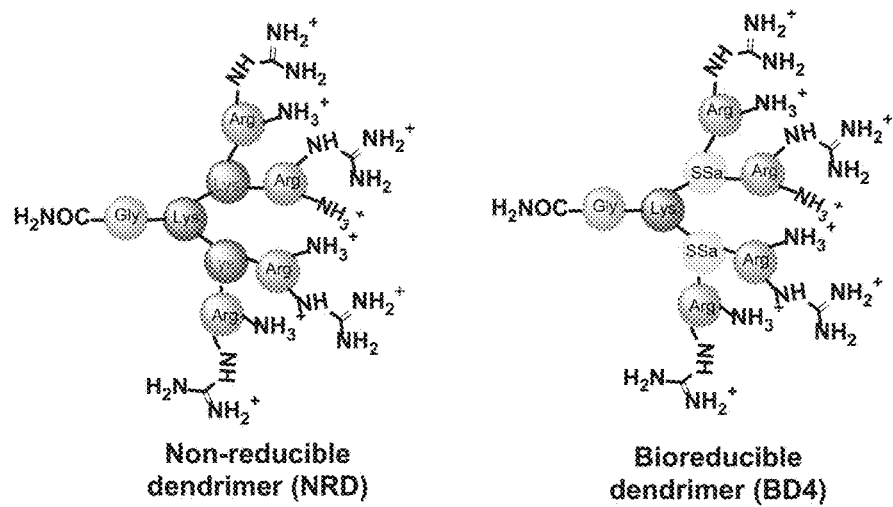
FIG. 1 is a representation of a non-reducible dendrimer and the analogous bioreducible dendrimer formed by incorporation of compounds of the first aspect.

According to a first aspect of the present invention, there is provided a compound of formula I, or a salt thereof:

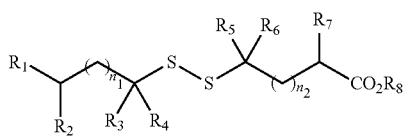

Formula I wherein, $R_1$ is selected from the group consisting of hydrogen, $R_9R_9'N$— and —$CO_2R_{10}$;

$R_2$ is selected from the group consisting of hydrogen and methyl;

$R_3$, $R_4$, $R_5$ and $R_6$ are independently selected from the group consisting of hydrogen and $C_1$ to $C_4$ alkyl, or, $R_3$ and $R_4$, when taken together along with the carbon to which they are bound, and/or $R_5$ and $R_6$, when taken together along with the carbon to which they are bound, can form a cyclic structure selected from the group consisting of $C_3$ to $C_5$ cycloalkyl, $C_3$ to $C_5$ oxygen-containing heterocycle, $C_3$ to $C_5$ nitrogen-containing heterocycle, and $C_3$ to $C_5$ sulphur-containing heterocycle, each of which may be substituted or unsubstituted;

$R_7$ is selected from the group consisting of hydrogen and $R_9R_9'N$—;

$R_8$ is selected from the group consisting of hydrogen, a counterion and a substituted or unsubstituted carboxylic acid protecting group;

$R_9$ and $R_9'$ are independently selected from the group consisting of hydrogen, substituted or unsubstituted $C_1$ to $C_6$ alkyl and a substituted or unsubstituted amine protecting group, or $R_9$ and $R_9'$ together form a substituted or unsubstituted amine protecting group;

$R_{10}$ is selected from the group consisting of hydrogen, a counterion and a substituted or unsubstituted carboxylic acid protecting group;

$n_1$ and $n_2$ are independently 0, 1, 2, 3, or 4; and with the provisos that, at least one of $R_3$, $R_4$, $R_5$ and $R_6$ is not hydrogen;

$R_1$ is not $NH_2$, BocHN or AcHN when all of the following are true: $R_2$ is hydrogen, $R_8$ is hydrogen or methyl, $n_1$ and $n_2$ are 0, $R_7$ is $R_9HN$—, $R_9$ is hydrogen or acetyl, $R_3$ and $R_4$ are hydrogen and $R_5$ and $R_6$ are methyl; and $R_8$ is not phenylisopropyl when all of the following are true: $n_1$ and $n_2$ are 0, $R_1$ is —$CO_2R_{10}$, $R_2$ is hydrogen, $R_3$ and $R_4$ are methyl, $R_5$ and $R_6$ are hydrogen, $R_7$ is $R_9HN$—, $R_9$ is Fmoc, and $R_{10}$ is hydrogen.

Preferably, $R_2$ is hydrogen.

In one embodiment of the first aspect, there is provided a compound of formula I, or a salt thereof:

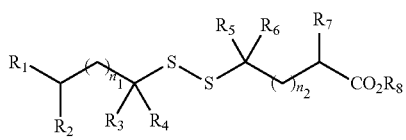

Formula I wherein, $R_1$ is selected from the group consisting of $R_9R_9'N$— and —$CO_2R_{10}$;

$R_2$ is hydrogen;

$R_3$, $R_4$, $R_5$ and $R_6$ are independently selected from the group consisting of hydrogen and substituted or unsubstituted $C_1$ to $C_4$ alkyl;

$R_7$ is $R_9R_9'N$—;

$R_8$ is selected from the group consisting of hydrogen, a counterion and a substituted or unsubstituted carboxylic acid protecting group;

$R_9$ and $R_9'$ are independently selected from the group consisting of hydrogen, substituted or unsubstituted $C_1$ to $C_6$ alkyl and a substituted or unsubstituted amine protecting group, or $R_9$ and $R_9'$ together form a substituted or unsubstituted amine protecting group;

$R_{10}$ is selected from the group consisting of hydrogen, a counterion and a substituted or unsubstituted carboxylic acid protecting group;

$n_1$ and $n_2$ are independently 0, 1, 2, 3, or 4; and with the provisos that, at least one of $R_3$, $R_4$, $R_5$ and $R_6$ is not hydrogen;

$R_1$ is not $NH_2$, BocHN or AcHN when all of the following are true: $R_8$ is hydrogen or methyl, $n_1$ and $n_2$ are 0, $R_7$ is $R_9HN$—, $R_9$ is hydrogen or acetyl, $R_3$ and $R_4$ are hydrogen and $R_5$ and $R_6$ are methyl; and $R_8$ is not phenylisopropyl when all of the following are true: $n_1$ and $n_2$ are 0, $R_1$ is —$CO_2R_{10}$, $R_3$ and $R_4$ are methyl, $R_5$ and $R_6$ are hydrogen, $R_7$ is $R_9HN$—, $R_9$ is Fmoc, and $R_{10}$ is hydrogen.

In one embodiment of the first aspect, there is provided a compound of formula II, or a salt thereof:

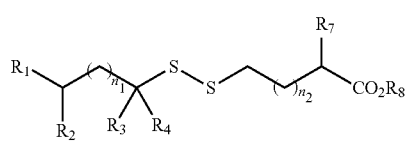

Formula II wherein, $R_1$, $R_2$, $R_3$, $R_4$, $R_7$, $R_8$, $R_9$, $R_9'$, $R_{10}$ and $n_1$ and $n_2$ are as described for formula I and wherein, $R_8$ is not phenylisopropyl when all of the following are true: $n_1$ and $n_2$ are 0, $R_1$ is $CO_2R_{10}$, $R_2$ is hydrogen, $R_3$ and $R_4$ are methyl, $R_7$ is $R_9HN$—, $R_9$ is Fmoc, and $R_{10}$ is hydrogen.

Preferably, $R_3$ and $R_4$ are substituted or unsubstituted $C_1$ to $C_4$ alkyl.

In one embodiment of the first aspect, there is provided a compound of formula III, or a salt thereof:

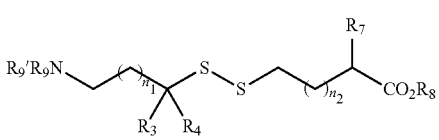

Formula III wherein, $R_3$, $R_4$, $R_7$, $R_8$, $R_9$, $R_9'$, and $n_1$ and $n_2$ are as described for formula I.

In one embodiment of the first aspect, there is provided a compound of formula III, or a salt thereof:

Formula III

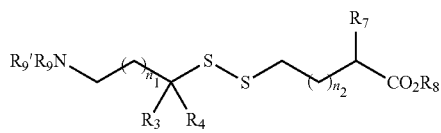

wherein, $R_8$, $R_9$, $R_9'$, and $n_1$ and $n_2$ are as described for formula I;

$R_3$ and $R_4$ are independently selected from substituted or unsubstituted $C_1$ to $C_4$ alkyl; and $R_7$ is $R_9R_9'N$—.

In one embodiment of the first aspect, there is provided a compound of formula IV, or a salt thereof:

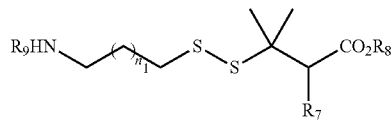

Formula IV wherein, $R_7$, $R_8$, $R_9$, $R_9'$ and $n_1$ are as described for formula I and wherein $R_9$ is not hydrogen, Boc or acetyl when all of the following are true: $n_1$ is 0, $R_7$ is $NH_2$ or NHAc, and $R_8$ is hydrogen or methyl.

In one embodiment, the compound of formula I, or salt thereof, is selected from the group consisting of:

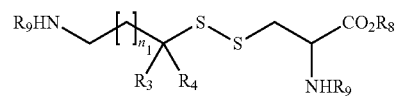

Formula V

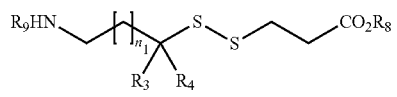

Formula VI

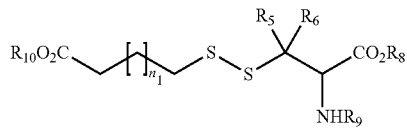

Formula VII

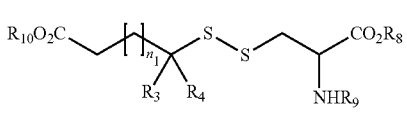

Formula VIII

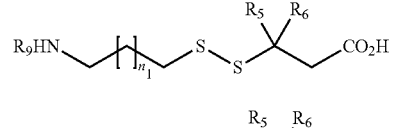

Formula IX

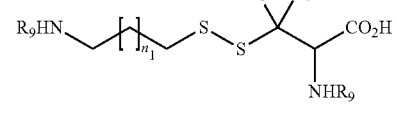

Formula X wherein, $R_3$, $R_4$, $R_5$, $R_6$, $R_8$, $R_9$, $R_{10}$ and $n_1$, as appropriate for each of formula V to X, are as described for formula I.

In one preferred embodiment, the compound of formula I, or salt thereof, is a compound of formula XI:

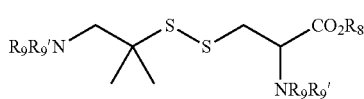

Formula XI wherein $R_8$ $R_9$ and $R_9'$ are as described for formula I.

In other words, in one embodiment of the first aspect, there is provided a compound of formula XI, or a salt thereof:

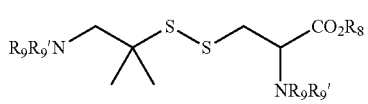

Formula XI wherein $R_8$ is selected from the group consisting of hydrogen, a counterion and a substituted or unsubstituted carboxylic acid protecting group; and $R_9$ and $R_9'$ are independently selected from the group consisting of hydrogen, substituted or unsubstituted $C_1$ to $C_6$ alkyl and a substituted or unsubstituted amine protecting group, or $R_9$ and $R_9'$ together form a substituted or unsubstituted amine protecting group.

In one embodiment, $R_9'$ are all hydrogen.

In one embodiment, the compound, or salt thereof, is a compound of formula XIa:

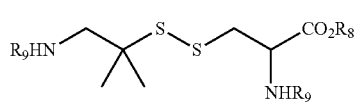

Formula XIa wherein $R_8$ is selected from the group consisting of hydrogen, a counterion and a substituted or unsubstituted carboxylic acid protecting group; and each $R_9$ is independently selected from the group consisting of hydrogen, $C_1$ to $C_6$ alkyl and a substituted or unsubstituted amine protecting group.

In one embodiment of the first aspect, there is provided a compound of formula XII, or a salt thereof:

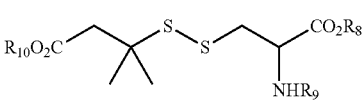

Formula XII wherein $R_8$ is selected from the group consisting of hydrogen, a counterion and a substituted or unsubstituted carboxylic acid protecting group;

$R_9$ is selected from the group consisting of hydrogen, substituted or unsubstituted $C_1$ to $C_6$ alkyl and a substituted or unsubstituted amine protecting group; and $R_{10}$ is selected from the group consisting of hydrogen, a counterion and a substituted or unsubstituted carboxylic acid protecting group.

In one embodiment of the first aspect, there is provided a compound of formula XIII, or a salt thereof:

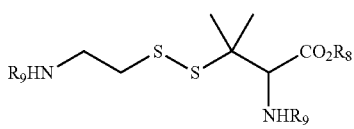

Formula XIII wherein $R_8$ is selected from the group consisting of hydrogen, a counterion and a substituted or unsubstituted carboxylic acid protecting group; and each $R_9$ is independently selected from the group consisting of hydrogen, substituted or unsubstituted $C_1$ to $C_6$ alkyl and a substituted or unsubstituted amine protecting group.

In one embodiment of the first aspect, there is provided a compound of formula XIV, or a salt thereof:

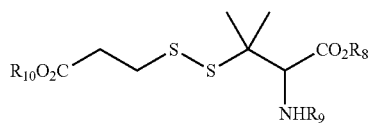

Formula XIV wherein $R_8$ is selected from the group consisting of hydrogen, a counterion and a substituted or unsubstituted carboxylic acid protecting group;

$R_9$ is selected from the group consisting of hydrogen, substituted or unsubstituted $C_1$ to $C_6$ alkyl and a substituted or unsubstituted amine protecting group; and $R_{10}$ is selected from the group consisting of hydrogen, a counterion and a substituted or unsubstituted carboxylic acid protecting group.

The following statements regarding the 'R' groups and 'n' chain lengths apply, as appropriate, to each of formula I to XIV.

In certain embodiments, $R_1$ is selected from the group consisting of $R_9R_9'N$— and —$CO_2R_{10}$, wherein $R_9$ and $R_9'$ are independently selected from the group consisting of hydrogen, alkoxycarbonyl, phenoxycarbonyl, benzyloxycarbonyl, acyl, alkyl, phenyl, benzyl, allyl, vinyl and sulfonyl, each of which groups may be substituted or unsubstituted; and $R_{10}$ is hydrogen or is a carboxylic acid protecting group selected from $C_1$-$C_6$ alkyl, benzyl including substituted benzyl such as nitrobenzyl, 2,6-disubstituted phenyl, substituted silyl including trialkylsilyl, trihaloalkyl, trialkoxyalkyl and oxazolyl, each of which carboxylic acid protecting groups may be substituted appropriately. In an embodiment, $R_9$ and $R_9'$ together form an amine protecting group which may be substituted or unsubstituted.

In certain embodiments, $R_2$ is hydrogen and $R_1$ is $R_9R_9'N$, wherein $R_9$ and $R_9'$ are independently selected from the group consisting of hydrogen, alkoxycarbonyl, phenoxycarbonyl, benzyloxycarbonyl, acyl, alkyl, phenyl, benzyl, methylidene, allyl, vinyl and sulfonyl, each of which groups may be substituted or unsubstituted. In an embodiment, $R_9$ and $R_9'$ together form an amine protecting group which may be substituted or unsubstituted.

In certain embodiments, $R_2$ is hydrogen and $R_1$ is —$CO_2R_{10}$, wherein $R_{10}$ is hydrogen or is a carboxylic acid protecting group selected from $C_1$-$C_6$ alkyl, benzyl including substituted benzyl such as nitrobenzyl, 2,6-disubstituted phenyl, substituted silyl including trialkylsilyl, trihaloalkyl, trialkoxyalkyl and oxazolyl, each of which carboxylic acid protecting groups may be substituted appropriately.

It will be understood by a person of skill in the art that certain carboxylic acid protecting groups recited for $R_8$ or $R_{10}$, such as, for example, trialkoxyalkyl and oxazolyl, will modify and mask the carboxylic acid group itself such that it is no longer represented by a simple —C(O)O-PG formula where PG is the relevant protecting group. For example, the oxazolyl group is formed in part from the carboxylic acid group to be protected. Nonetheless, it will be understood that all such groups can be removed or hydrolysed or otherwise converted back to the carboxylic acid group and so are considered to be within the scope of the carboxylic acid protecting groups recited for formula I or XIV, above.

In certain embodiments, $R_2$ is hydrogen.

In certain embodiments, $R_3$, $R_4$, $R_5$ and $R_6$ are independently selected from the group consisting of methyl, ethyl, propyl, isopropyl, n-butyl, sec-butyl, isobutyl, tert-butyl, or, $R_3$ and $R_4$, when taken together along with the carbon to which they are bound, and/or $R_5$ and $R_6$, when taken together along with the carbon to which they are bound, can be cyclopropyl, cyclobutyl or cyclopentyl.

In certain embodiments, either $R_3$ and $R_4$ or $R_5$ and $R_6$ are the same.

In certain embodiments, when $R_3$ and $R_4$ are non-hydrogen then $R_5$ and $R_6$ are hydrogen.

In certain embodiments of the compound of formula I to XIV, either $R_3$ and $R_4$ together or $R_5$ and $R_6$ together are methyl, ethyl or propyl. That is, either $R_3$ and $R_4$ when taken together along with the carbon to which they are bound, can form a gem-dimethyl, gem-diethyl or gem-dipropyl group; or $R_5$ and $R_6$ when taken together along with the carbon to which they are bound, can form a gem-dimethyl, gem-diethyl or gem-dipropyl group. In certain embodiments, either $R_3$ and $R_4$ when taken together along with the carbon to which they are bound, can form a gem-dimethyl group; or $R_5$ and $R_6$ when taken together along with the carbon to which they are bound, can form a gem-dimethyl group.

In certain embodiments, $R_3$ and $R_4$ are independently selected from methyl, ethyl and propyl; and $R_5$ and $R_6$ are hydrogen. Preferably, in certain embodiments, $R_3$ and $R_4$ are methyl; and $R_5$ and $R_6$ are hydrogen.

In certain embodiments, $R_5$ and $R_6$ are independently selected from methyl, ethyl and propyl; and $R_3$ and $R_4$ are hydrogen. Preferably, in certain embodiments, $R_5$ and $R_6$ are methyl; and $R_3$ and $R_4$ are hydrogen.

In certain embodiments, $R_7$ is selected from the group consisting of hydrogen and $R_9HN$—, and $R_9$ selected from the group consisting of hydrogen, alkoxycarbonyl, phenoxycarbonyl, benzyloxycarbonyl, acyl, alkyl, phenyl, benzyl, allyl, vinyl and sulfonyl, each of which groups may be substituted or unsubstituted.

In certain embodiments, $R_8$ is selected from the group consisting of hydrogen and a carboxylic acid protecting group selected from $C_1$-$C_6$ alkyl, benzyl including substituted benzyl such as nitrobenzyl, 2,6-disubstituted phenyl, substituted silyl including trialkylsilyl, trihaloalkyl, trialkoxyalkyl and oxazolyl, each of which carboxylic acid protecting groups may be substituted appropriately.

In certain embodiments, $R_9$ and $R_9'$ are independently selected from the group consisting of hydrogen, alkoxycarbonyl, phenoxycarbonyl, benzyloxycarbonyl, acyl, alkyl, phenyl, benzyl, allyl, vinyl and sulfonyl, each of which groups may be substituted or unsubstituted.

In certain embodiments, $R_9$ and $R_9'$, when taken together, form an amine protecting group, such as methylidene, benzylidene or phthaloyl, each of which may be substituted or unsubstituted. The person skilled in the art will appreciate that a number of amino protecting groups can be utilized in this manner, and the above list is not an exhaustive list.

$R_9$ and $R_9'$ have been described herein for multiple —$NR_9R_9'$ groups or —$NHR_9$ groups, and it will be appreciated that each $R_9$ and $R_9'$ group is independently selected from the list provided. As such, the $R_9$ and $R_9'$ groups in the same compound may be the same or different moieties. For instance, the $R_9$ and $R_9'$ moieties for $R_7$ may be different or the same as the $R_9$ and $R_9'$ moieties for $R_1$ (where applicable).

In certain embodiments of formula I to XIV, as appropriate, $R_9$ and $R_9'$ are independently selected from the group consisting of hydrogen, fluorenylmethoxycarbonyl (Fmoc), t-butyloxycarbonyl (Boc), benzyloxycarbonyl (carboxybenzyl, Cbz), p-methoxybenzyloxycarbonyl (Moz, MeOZ), formyl, acetyl (Ac), trifluoroacetyl, trichloroacetyl, benzoyl (Bz), p-methoxyphenyl (PMP), benzyl (Bn), p-methoxybenzyl (PMB), 3,4-dimethoxybenzyl (DMPM), 2,4-dimethoxybenzyl (Dmb), triphenylmethyl (trityl, Tr), 4-methyltriphenylmethyl (4-methyltrityl, Mtt), 4-methoxytriphenylmethyl (4-methoxytrityl, Mmt), diphenylmethylene, N-1-(4,4-dimethyl-2,6-dioxocyclohexylidene)ethyl (Dde), benzene sulfonyl, p-toluenesulfonyl (tosyl) and 2,2,4,6,7-pentamethyldihydrobenzofuran-5-sulfonyl (Pbf), each of which groups may be substituted or unsubstituted.

In other preferred embodiments of formula I to XIV, as appropriate, $R_9$ and $R_9'$ are independently selected from the group consisting of hydrogen, fluorenylmethoxycarbonyl (Fmoc), t-butyloxycarbonyl (Boc), benzyloxycarbonyl (carboxybenzyl, Cbz), N-1-(4,4-dimethyl-2,6-dioxocyclohexylidene)ethyl (Dde) and 4-methyltriphenylmethyl (4-methyltrityl, Mtt), each of which groups may be substituted or unsubstituted.

In an embodiment, at least one $R_9$ or $R_9'$ is H. In one embodiment, all $R_9'$ are H. In another embodiment, at least one $R_9$ is H. In another embodiment, all $R_9$ are H.

In certain embodiments, $R_{10}$ is hydrogen or is a carboxylic acid protecting group selected from $C_1$-$C_6$ alkyl, benzyl, 2,6-disubstituted phenyl, $C_1$-$C_6$ trialkylsilyl, trialkoxyalkyl and oxazolyl, each of which may be substituted or unsubstituted.

In preferred embodiments, $n_1$ and $n_2$ are independently 0, 1, or 2. Suitably, $n_1$ and $n_2$ are 1. Preferably, $n_1$ and $n_2$ are 0.

The amine protecting group and carboxylic acid protecting groups discussed herein may be selected from the wide array of standard protecting groups, these typically being commercially available. Texts forming part of the available references for such protecting groups and strategies for their use in synthesis include Greene's Protective Groups in Organic Synthesis: $5^{th}$ Edition; and "Protecting Groups" by Philip Kocienski: $3^{rd}$ Edition, each of which are hereby incorporated by reference in its entirety for all purposes.

In certain embodiments of any one of formulae I to XIV, as appropriate, the amine protecting group can be selected from the group consisting of alkoxycarbonyls, phenoxycarbonyls, benzyloxycarbonyls, acyls, alkyls, phenyls, benzyls, methylidenes, allyls, vinyls, phthaloyls, sulfonyls, and derivatives thereof, each of which groups may be substituted or unsubstituted.

In certain embodiments of any one of the above formulae I to XIV, the amine protecting group (and therefore $R_9$ and $R_9'$) can be selected from the group consisting of fluorenylmethoxycarbonyl (Fmoc), t-butyloxycarbonyl (Boc), benzyloxycarbonyl (carboxybenzyl, Cbz), p-methoxybenzyloxycarbonyl (Moz, MeOZ), formyl, acetyl (Ac), trifluoroacetyl, trichloroacetyl, benzoyl (Bz), p-methoxyphenyl (PMP), benzyl (Bn), p-methoxybenzyl (PMB), 3,4-dimethoxybenzyl (DMPM), 2,4-dimethoxybenzyl (Dmb), triphenylmethyl (trityl, Tr), 4-methyltriphenylmethyl (4-methyltrityl, Mtt), 4-methoxytriphenylmethyl (4-methoxytrityl, Mmt), diphenylmethylene, N-1-(4,4-dimethyl-2,6-dioxocyclohexylidene)ethyl (Dde), benzene sulfonyl, p-toluenesulfonyl (tosyl), 2,2,4,6,7-pentamethyldihydrobenzofuran-5-sulfonyl (Pbf), methoxycarbonyl, ethoxycarbonyl, adamantyloxycarbonyl, allyloxycarbonyl, 2,4-dichlorobenzyloxycarbonyl, t-butyl, allyl, 4-nitrobenzenesulfonyl (nosyl) and 4-bromobenzenesulfonyl (brosyl), each of which groups may be substituted or unsubstituted.

In embodiments of any one of formulae I to XIV, the carboxylic acid protecting group can be selected from $C_1$-$C_6$ alkyl, benzyl, 2,6-disubstituted phenyl, substituted silyl including alkyl substituted silyl, trialkoxyalkyl and oxazolyl, each of which may be substituted or unsubstituted.

In certain embodiments of any one of the above formulae I to XIV, as appropriate, the carboxylic acid protecting group (and therefore $R_8$ or $R_{10}$) can be selected from the group consisting of methyl, ethyl, tert-butyl, benzyl, 2,6-dimethylphenyl, 2,6-diisopropylphenyl, 2,6-di-t-butylphenyl, trimethoxy alkyl, triethoxy alkyl, trimethyl silyl and 1,3-oxazoline, each of which groups may be substituted or unsubstituted.

In certain embodiments, the compound of formula XIV can have $R_9$ and $R_9'$ independently selected from the group consisting of hydrogen, fluorenylmethoxycarbonyl (Fmoc), t-butyloxycarbonyl (Boc), benzyloxycarbonyl (carboxybenzyl, Cbz), N-1-(4,4-dimethyl-2,6-dioxocyclohexylidene) ethyl (Dde) and 4-methyltriphenylmethyl (4-methyltrityl, Mtt), each of which may be substituted or unsubstituted, each of which may be in combination with any of the following options for $R_8$ which can be hydrogen or a carboxylic acid protecting group selected from $C_1$-$C_6$ alkyl, benzyl, 2,6-disubstituted phenyl, substituted silyl, trialkoxyalkyl and oxazolyl, each of which may be substituted or unsubstituted.

It can be appreciated that the disulfide bond containing compound of the first aspect can be synthesised, sold or otherwise provided in an unprotected form, i.e. whereby the relevant amino and/or carboxylic acid groups are in the —$NH_2$ and —$CO_2H$ forms. Alternatively, the same core compound can be synthesised, sold or otherwise provided in a protected form with, for example, the relevant amino and/or carboxylic acid groups protected, typically by well-known orthogonal protecting groups. When the core compound is within the structure of any of formula I to XIV then all such protected analogues of the compound are also explicitly considered to be included.

In one embodiment, when the compound of the first aspect is a salt it is a pharmaceutically acceptable salt. Common pharmaceutically acceptable salts are well known in the art and can be prepared, for example, by simple salification procedures.

Referring now to terminology used generically herein, the term "alkyl" means an optionally substituted straight or branched chain alkyl substituent containing from, for example, 1 to about 6 carbon atoms, 1 to about 5 carbon atoms, 1 to about 4 carbon atoms, from 1 to about 3 carbon atoms, or from 1 to 2 carbon atoms. Examples of such substituents considered to be included within these ranges include methyl, ethyl, propyl, isopropyl, n-butyl, sec-butyl, isobutyl, tert-butyl, pentyl, isoamyl, hexyl, and the like. The number of carbons referred to relates to the carbon backbone and carbon branching but does not include carbon atoms belonging to any further substituents, for example the carbon atoms of an alkoxy substituent branching off the main carbon chain.

The term "cycloalkyl" refers to optionally substituted saturated mono-cyclic carbon groups. Where appropriate, the cycloalkyl group may have a specified number of carbon atoms, for example, $C_3$-$C_5$ cycloalkyl is a carbocyclic group having 3, 4 or 5 carbon atoms. Non-limiting examples may include cyclopropyl, cyclobutyl and cyclopentyl.

Whenever a range of the number of atoms in a structure is indicated (e.g., a $C_1$-$C_6$, $C_1$-$C_5$, $C_1$-$C_4$, $C_1$-$C_3$, $C_1$-$C_2$, or $C_2$-$C_6$, $C_2$-$C_5$, $C_2$-$C_4$, $C_2$-$C_3$, alkyl, etc.), it is specifically contemplated that any sub-range or individual number of carbon atoms falling within the indicated range also can be used. Thus, for instance, the recitation of a range of 1-6 carbon atoms (e.g., $C_1$-$C_6$), 1-5 carbon atoms (e.g., $C_1$-$C_5$), 1-4 carbon atoms (e.g., $C_1$-$C_4$), 1-3 carbon atoms (e.g., $C_1$-$C_3$), as used with respect to any chemical group (e.g., alkyl etc.) referenced herein encompasses and specifically describes 1, 2, 3, 4, 5, 6, carbon atoms, as appropriate, as well as any sub-range thereof.

The term "heterocycle" as used by itself or as part of another group refers to saturated and partially unsaturated (e.g., containing one or two double bonds) cyclic groups containing one, two, or three rings having from three to ten ring members (i.e., a 3- to 10-membered heterocycle) wherein at least one atom of the rings is a heteroatom. Each heteroatom is independently selected from the group consisting of oxygen, sulfur, including sulfoxide and sulfone, and/or nitrogen atoms, which can be oxidized or quaternized. The heterocycle may be substituted or unsubstituted.

The term "pharmaceutically acceptable salt", as used herein, refers to salts which are toxicologically safe for systemic or localised administration such as salts prepared from pharmaceutically acceptable non-toxic bases or acids including inorganic or organic bases and inorganic or organic acids. The pharmaceutically acceptable salts may be selected from the group consisting of alkali and alkali earth, ammonium, aluminium, iron, amine, glucosamine, chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, palmoate, piperazine, pectinate and S-methyl methionine salts and the like.

The term "counterion" as used herein refers to an ion which accompanies the otherwise ionic group with which it is associated to thereby achieve electrical neutrality. It should be recognized that the particular counterion forming a part of any group listed in relation to any of the structural formulae described herein is usually not of a critical nature, so long as the counterion does not contribute undesired qualities to the salt as a whole. By way of example, suitable counterions for a carboxylic acid group may be selected from, but are not limited to, $H^+$, $Na^+$, $K^+$ and the like. Such counterions are well known to a person skilled in the art of synthetic organic chemistry.

The term "substituted" used herein means any of the groups described herein (e.g., alkyl, cycloalkyl, heterocycle, carboxylic acid protecting group, amine protecting group) wherein at least one hydrogen atom is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group.

It can be appreciated that the compounds of the first aspect can be used as amino acid-like building blocks when it is desirable to include a disulfide linkage within the synthesised structure. It is an advantage of the present compounds that, as the disulfide bond is a pre-generated component of the building block which is additionally provided with one or more amino and carboxylic acid groups, the disulfide bond, via the appropriate pendant groups on the compound, can be integrated into a peptide (i.e. cyclic or linear) or other structure (i.e. macromolecules or dendrimers) using standard amide coupling conditions rather than the common prior art approach using oxidising conditions and costly cross-linking reagents. In this regard, compounds with a RHN or a $CO_2R$ group in the $R_1$ position can allow the S—S bond to be incorporated into a cyclic structure for enhanced stability.

Without being bound by theory, the provision of, in some embodiments, a single or gem alkyl or a single cycloalkyl moiety at either the $R_3$/$R_4$ or $R_5$/$R_6$ carbons, for example wherein the $R_3$/$R_4$ groups when taken together along with the carbon to which they are bound form a gem dimethyl group, is postulated to stabilise the disulfide bond by the induction of electrons into that bond. This reduces the potential for base (and acid) catalysed cleavage of the disulfide bond, making it suitable for SPPS and SPOS (solution phase organic synthesis). In vivo, the disulfide bond will be stable to extracellular reducing conditions (low µM concentrations of glutathione (GSH)), but it is reduced and cleaved in the intracellular reducing conditions (high mM GSH). This characteristic means that the disulfide bonds, introduced via the compounds of the first aspect, within a peptide or dendrimer or drug delivery vehicle or probe could be selectively cleaved within cells by thiol-disulfide exchange to degrade the structure and release entrapped cargo, in the manner of a bio-reducible peptide dendrimer, or the disulfide bonds could be cleaved to release a conjugated therapeutic or diagnostic.

Further, without being bound by theory, it is postulated that compounds of the first aspect which have a gem dimethyl, or similar group, immediately adjacent the disulfide bond, and which additionally have only a terminal amino moiety on the other side of the gem substituted carbon are particularly suitable in terms of stability and/or structure to enable efficient incorporation into peptide structures, dendrimers and drug delivery vehicles using standard SPPS/SPOS chemistries. In this regard, such compounds of the first aspect can be particularly useful for forming peptide structures, dendrimers and delivery vehicles that afford the above preferential reduction selectivity.

Other compounds of the first aspect having, for example, a carboxylic acid and amino group as the terminal moieties on the side of the gem substituted carbon opposite the disulfide bond, are also useful as a means of introducing a disulfide bond into a peptide and/or dendrimer structure in situ, without oxidising conditions, and, without wishing to be bound by any particular theory, are believed to provide a degree of selectivity in reduction. Dendrimeric structures, due to their branched flexible nature, are postulated to accommodate the gem substituted steric bulk within their core and not being therapeutic entities in their own right which is expected to have little impact on their ability to complex with a bioactive molecule.

As mentioned herein, the compounds of the first aspect can form part of the structure of linear peptides, cyclic peptides, macromolecules and/or dendrimers. It is postulated that compounds of the first aspect where $R_3$ and $R_4$ or $R_5$ and $R_6$ are methyl, ethyl or propyl (in particular, $R_3$ and $R_4$ are methyl) impart suitable stability that allows the compound to be incorporated into linear peptides, cyclic peptides, macromolecules and/or dendrimers by SPPS or SPOS. This is a significant advantage as the S—S bond can be introduced easily and without the use of cross-linking reagents.

Furthermore, the pre-formed S—S bond may avoid/minimize purification complications that arise from solution phase S—S bond formation. This is particularly the case when the cyclic peptide synthesis of the cyclic portion is formed via amide formation.

The amino acid functionality and the stability imparted by the methyl groups in the $R_3$ and $R_4$ positions allows for the incorporation of a compound of the first aspect into a peptide structure through SPPS or SPOS. Additionally, the adjacent steric groups in the $R_3$ and $R_4$ positions are believed to tailor bioreduction of the S—S bond to intracellular conditions and are less susceptible to bioreduction in extracellular conditions.

A dendrimer that comprises a compound of formula XI or XIa are particularly useful as the side chain amino functionality allows for extension through SPPS or SPOS; or, alternatively, covalently attaching therapeutics/targeting ligands. In an embodiment, the invention resides in a dendrimer that is produced using a compound of formula XI or XIa.

Furthermore, another advantage is that a peptide or dendrimer that comprises a compound of formula XI or XIa that undergoes bioreduction does not form penicillamine. Penicillamine has multiple toxicities and is known to have toxic side effects from in vivo degradation. It is believed that a dendrimer comprising a compound of formulae V, VIII, XI, XIa or XII does not form penicillamine during bioreduction and avoids these toxic side effects.

In some embodiments, for stability of the disulfide bond, $n_1$ and $n_2$ are 0.

Compounds of formula I to XIV can lend themselves to different uses within the formation of a peptidic or dendrimeric structure. For example, compounds of formula VI and IX can be suitable for inclusion as an end of peptide chain residue from which to form a bridging or cyclic structure or to which a bioactive can be attached for subsequent delivery and release.

In general terms, the compound of the first aspect can be incorporated into a growing peptide backbone, for example via the α-$R_9$NH (i.e. $R_7$) and $CO_2H$ groups, such as for compounds of formula XI. These amine and carboxylic acid functional groups can be coupled with the appropriate amine or carboxylic acid function group on another amino acid to form an amide bond, and thus incorporate the compound of the first aspect into a peptide sequence. The side-chain $R_9NH$ (i.e. $R_1$) on the compound of formula XIa can subsequently be deprotected and coupled, via an amide bond, to, for example, a $CO_2H$ group of another α-amino acid residue, to form a branched peptide structure or dendrimer; or to a side-chain $CO_2H$ group on an aspartic or glutamic acid residue within the peptide to form a cyclised or —S—S— bridged peptide.

It is envisaged that the compound of Formula I-XIV can be lipidated. In on embodiment, a lipidated compound of Formula I-XIV refers to a product formed when hydrophobic molecules are added to the compound. In an embodiment, the compound of the first aspect has at least one bond to an atom replaced by a bond or connection to a lipid. It is postulated that compounds of the first aspect (where applicable) can be used to form bioreducible phospholipids. The advantages of lipidating the compound of formula I—XIV are discussed in more detail hereinafter.

The compounds of the first aspect can be synthesised by more than one approach. One route is described in the examples section. Scheme 1 and Scheme 2, below, indicate routes by which compounds of formula I to XIV can be accessed. Broadly, Scheme 1 employs steps of (i) addition of non-hindered thiols and $Et_3N$; (ii) addition of hindered thiols; and (iii) ester conversion into acids. Scheme 2, while not optimised for improved yields, has the advantage of being a one pot synthesis with the reaction driven by $Et_3N$, which generates a thiolate anion so initiating (non-specific) disulfide bond formation. Method B was employed for a number of the compound syntheses described in the experimental section.

Scheme 1 - Method A

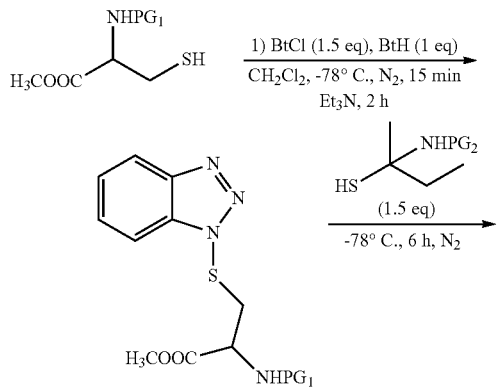

-continued

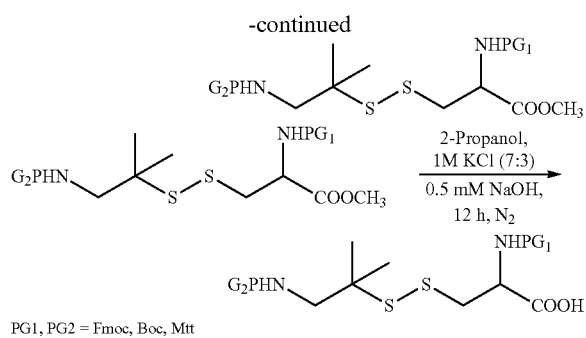

PG1, PG2 = Fmoc, Boc, Mtt

Scheme 2 - Method B

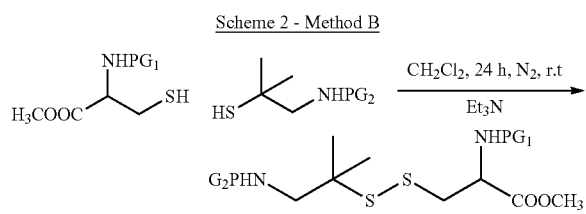

The results obtained with certain protecting group (PG) strategies are indicated in table 1, below.

TABLE 1

Yields for synthetic approaches to compounds of formula 1 using synthetic pathways A and B (yields not optimized for method B where dimerization of starting materials results in more challenging separation of the target molecule).

| | | Yield | |
|---|---|---|---|
| Entry | Protecting Groups | Method-A | Method-B |
| 1 | PG1 = Boc<br>PG2 = Boc | 72% | 15% |
| 2 | PG1 = Fmoc<br>PG2 = Fmoc | 58% | 40% |
| 3 | PG1 = Fmoc<br>PG2 = Boc | 70% | 52% |
| 4 | PG1 = Fmoc<br>PG2 = Mtt | 55% | 42% |

According to a second aspect, the invention resides in a method of forming a peptide structure comprising the step of reacting a compound of the first aspect with a complimentary amino acid or bioactive molecule.

In one embodiment, the peptide structure is a peptide chain or cyclic peptide.

In a further embodiment, the peptide structure is a peptide-based dendrimer.

In one embodiment, the peptide structure comprises a bioactive molecule. As used herein "bioactive molecule" refers a molecule which initiates a biological response, e.g., through enzymatic activity or by binding to a receptor. In one embodiment, the bioactive molecule is selected from the group consisting of genetic material, peptide therapeutics, small molecule drugs, drug conjugates, antibodies and ionic compounds.

The reaction can be under standard peptide coupling conditions and the particular approach, as can be appreciated by one of skill in the art, can be dictated by the structure and protecting groups of the two reactants.

By way of example, the cyclic structure into which the compound of the first aspect becomes incorporated may be a known cyclic peptide. It can be appreciated that certain compounds of the first aspect lend themselves more easily to formation of a cyclic peptide than others. Such compounds can have amino and carboxylic acid backbone groups to allow for incorporation into the peptide chain and additionally provide a further functionality, likely amino or carboxylic acid, which can be used to form an amide bond with a remote amino acid to thereby generate a cyclic peptide structure. Compounds of formula V, VII, VIII, X and XI-XIV may be particularly suitable in this regard.

According to a third aspect, the invention resides in a peptide structure comprising a compound of the first aspect. In other words, the invention resides in a peptide structure produced using a compound of the first aspect.

The peptide structure can be a linear peptide, cyclic peptide or dendrimeric structure.

The peptide structure can further comprise a bioactive molecule bonded to or otherwise associated with the peptide structure.

The bioactive molecule can be as described for the second aspect.

It can be appreciated by the person of skill in the art that the incorporation of the compound of the first aspect into, for example, a peptide chain can mean the compound of the first aspect no longer displays a structure corresponding exactly to the formulae I to XIV but rather is modified, at least at one group, by reaction with the peptide chain amino acids to form an amide bond. Therefore, in the aspects of the invention wherein the compounds of the first aspect are complexed to or bonded with a further compound or structure (e.g., an amino acid, a peptide sequence, a bioactive molecule, a lipid, a tag, or a probe), reference to a compound of the first aspect includes such modified structures taking into account attachment, e.g., to the peptide structure or other entity. In this regard, the structure corresponding to formulae I to XIV is modified by at least one of $R_8$ and $R_9$ being independently replaced by a bond to an amino acid, a peptide sequence, a bioactive molecule, a lipid, a tag or a probe. In other words, the compound of formulae I to XIV may be present in a compound wherein at least one of the $R_8$ and $R_9$ are independently replaced with a bond to the structure of the compound.

In embodiments wherein the peptide structure is a dendrimer then the dendrimer can be synthesised with or using one or more compounds of the first aspect either incorporated within the dendrimer branches, that is, not at the terminus of any branch, or they can be incorporated at the terminal portion of the dendrimer branches.

Figure 2:
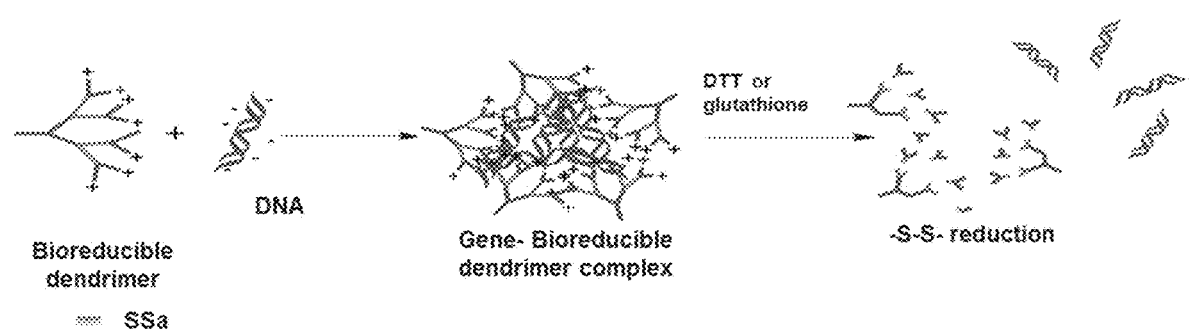
FIG. 2 is a schematic representation of the complexation and subsequent release of DNA from a bioreducible dendrimer.

One particular example of such an 'internal' dendrimer is shown in FIG. 1 wherein a short dendrimer is shown, firstly with a lysine in each branch between the first lysine and the arginine amino acids to form a non-reducible dendrimer which is stable to intracellular glutathione and, secondly, wherein the lysines in the branches have been replaced by compounds of the first aspect, for example compounds of formula XI or XIa. The latter dendrimer structure is bioreducible in that the disulfide bonds of the compounds of the first aspect can be reduced by intracellular glutathione so the dendrimer will effectively degrade. When a bioactive molecule is complexed with such bioreducible dendrimers then degradation of the dendrimer effects intracellular release of the bioactive. This process of complexation, degradation through reduction and release of bioactive is represented schematically in FIG. 2. The bioactive, by way of one non-limiting example only, can be genetic material. The dendrimer structures shown in the figures are charged structures without a counterion for convenience. However, the person skilled in the art will appreciate that these dendrimer structures can be formed with any counterion. Preferably, the counterion is a pharmaceutically acceptable counterion. Additionally, the dendrimer structure may be present in the form of a neutral compound. The charged dendrimer structure may have at least about 10%, at least about 20%, at least about 30%, at least about 40%, at least about 50%, at least about 60%, at least about 70%, at least about 80%, at least about 90%, at least about 95%, or 100% of the lone pair of electrons on the nitrogen(s) replaced by a bond to hydrogen.

To form the bioreducible dendrimer of FIG. 1 a compound of formula XI or XIa has been coupled to a Lys amino acid at each of its $\alpha$-NH$_2$ and side-chain NH$_2$ groups. The $\alpha$-R$_9$NH (i.e. R$_7$) and side-chain R$_9$NH (i.e. R$_1$) of both compounds of formula XI or XIa are then sequentially deprotected and coupled to Arg amino acids.

Figure 3:
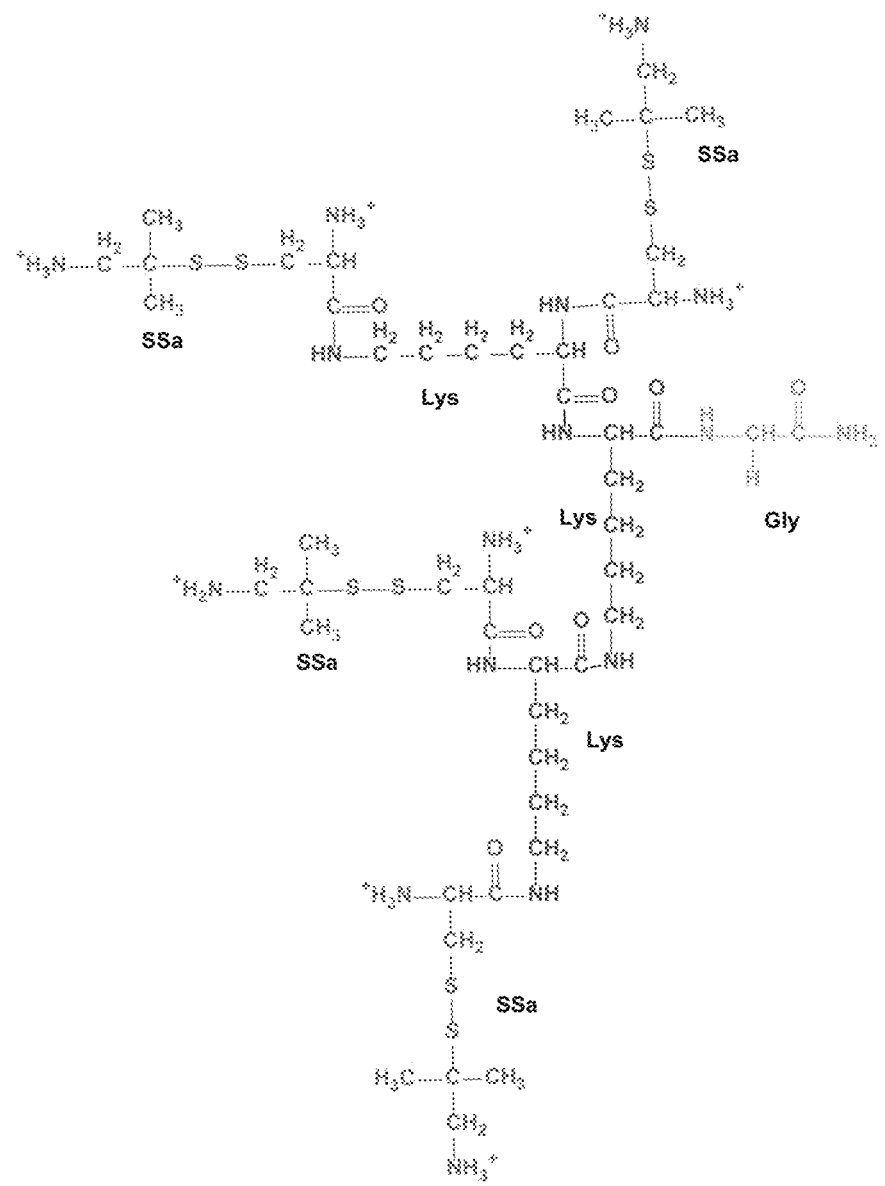
FIG. 3 is a structural representation of an 8+ bioreducible dendrimer comprising compounds of Formula I.

An example of a dendrimer with terminal disulfide bond containing compounds of the first aspect is shown in the sketched structure of an 8+ dendrimer in FIG. 3 wherein 'SSa' refers to a compound of the first aspect, such as formula XI or XIa, and the other amino acids in the structure are identified. To achieve this, the compound of formula XI or XIa is coupled to each of the $\alpha$-NH$_2$ and side-chain NH$_2$ groups of a Lys amino acid. In this case, the side-chain R$_9$NH (i.e. R$_1$) and the $\alpha$-NH$_2$ of the compounds of formula XI or XIa are not coupled to further amino acids (that is, the SSa amino acid is not currently conjugated and so presents a free terminal —NH$_2$ group) and therefore can potentially be used to physically conjugate bioactive molecules.

Figure 4:
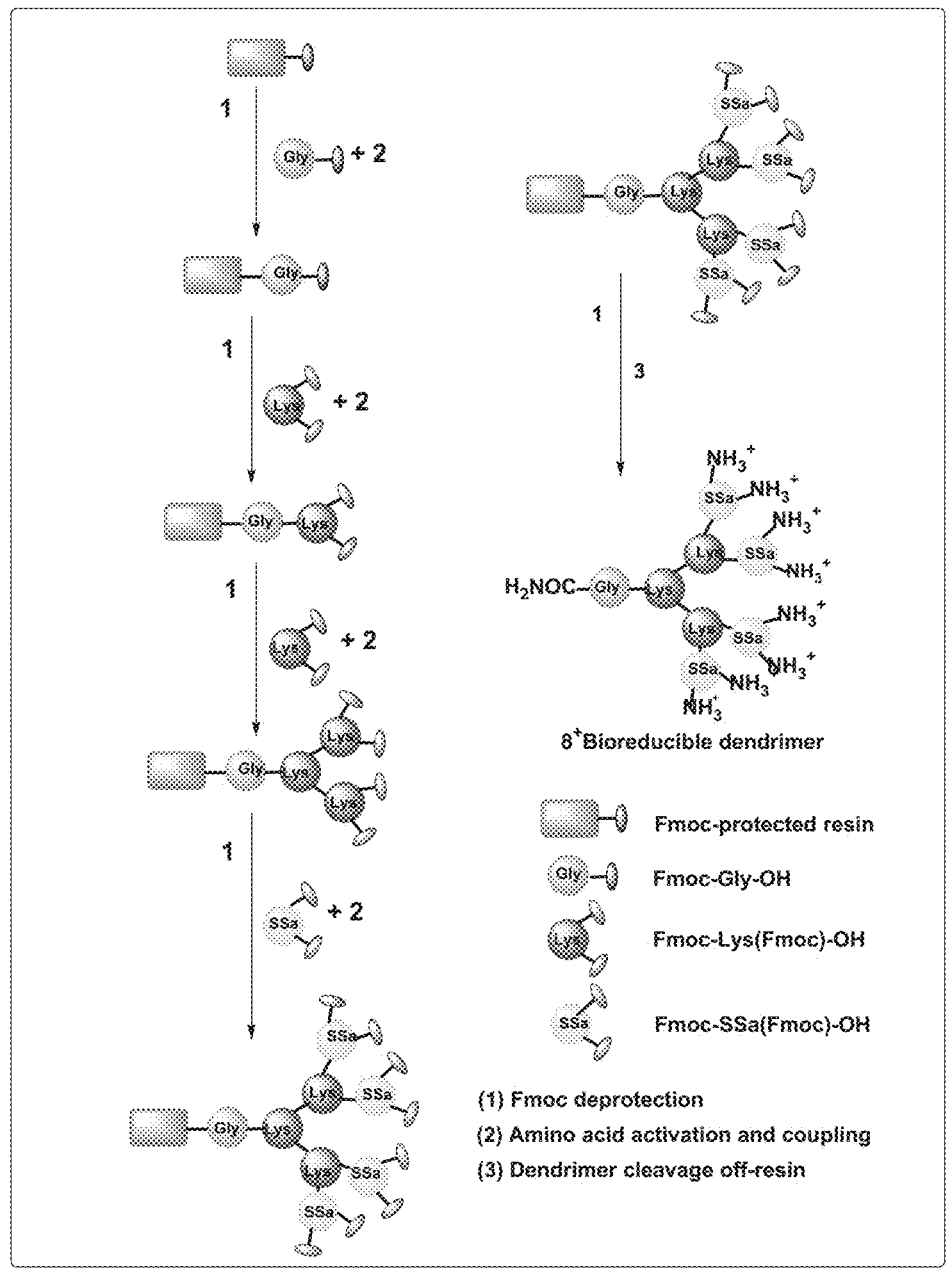
FIG. 4 is a schematic representation of the synthesis of an asymmetric bioreducible dendrimer.

The peptide structures of the third aspect, comprising the incorporated compound of the first aspect, can be synthesised by standard peptide coupling techniques. In other words, the peptide structure of the third aspect is produced using the compound of the first aspect. One such approach is exemplified schematically in FIG. 4 resulting in terminal compounds of the first aspect presenting free amino groups to which a bioactive molecule can be complexed or bonded.

The dendrimer of the third aspect can present any number of generations and can have internal compounds of the first aspect incorporated into any one or more of those generations, which can be particularly useful when the intention, upon reduction, is degradation of the dendrimer.

According to a fourth aspect, the invention resides in a delivery vehicle comprising a macromolecule, the macromolecule comprising a compound of the first aspect, and wherein the macromolecule is complexed with or bonded to a bioactive molecule. In other words, the macromolecule is produced using the compound of the first aspect.

According to a fifth aspect, the invention resides in a method of delivering a bioactive molecule to a target site in a mammal including the step of providing a delivery vehicle of the fourth aspect to the mammal to thereby deliver the bioactive molecule.

In one embodiment, the fifth aspect further includes the step of cleaving a disulfide linkage within the delivery vehicle to release the bioactive molecule.

In embodiments of the fourth and fifth aspects, the macromolecule can be selected from the group consisting of a protein, a peptide, a dendrimer, a polymer and a lipid or any particle derived therefrom.

In some embodiments, it is postulated that lipidated dendrimers can enhance its delivery to target cells. In one embodiment, the dendrimer is lipidated. Additionally, it is believed that lipids can act as targeting ligands that enhance cell-specific recognition. For instance, it is postulated that inclusion of certain lipids allow the dendrimer to target a specific tissue cell receptor to enable the bioactive molecule to subsequently interact with the desired target cells when subsequently released.

Examples of the macromolecule are proteins such as antibodies, a range of biocompatible polymers such as PEG, dendrimers constructed from a range of amino acids including Gly, Lys, Arg, Glu and the like and including a compound of the first aspect, and lipids including linear $C_6$-$C_{18}$ lipids, including saturated and unsaturated forms, liposomes, as well as steroids such as cholic acid and cholesterol. Lipidated structures comprising a compound of the first aspect can be used to form bioreducible liposomes and/or micelles and/or solid lipid particles or a variety of other such micro or nanodelivery systems known in the art. The liposomes, micelles, and/or solid lipid particles may be in the form of a solution or suspension. Alternatively, the liposomes, micelles, and/or solid lipid particles may be in the form of a powder. The powder may be formed by freeze drying or lyophilisation. The liposomes, micelles, and/or solid lipid particles may be stored as a powder prior to reconstitution.

In one embodiment, the macromolecule comprises a compound of formula (XI). In one embodiment, the macromolecule is a bioreducible liposome that comprises a compound of the first aspect that is lipidated. In an embodiment, the macromolecule has at least one bond replaced by a bond or connection to a lipid. It will be appreciated that the lipidated compound of the first aspect may comprise at least one functional group that is lipidated. In an embodiment, the lipidated compound of the first aspect may comprise two functional groups being lipidated. In this embodiment, at least one functional group accommodates a phosphate group. Such structures can act as delivery vehicles and benefit from the previously discussed active intracellular release of, for example, drugs, genes or proteins from the compound of formula I. A range of nanoparticles may also be suitable.

In one embodiment, the bioactive molecule is complexed with the macromolecule. For example, if the macromolecule is a dendrimer then the bioactive molecule can be attracted to charges displayed by certain of the functional groups displayed by the dendrimer. It will be appreciated that a bioactive molecule can be complexed with one or more dendrimers. The dendrimer branches can therefore provide an anionic or cationic charge which is capable of complexing with the bioactive molecule carrying an opposite charge. In one embodiment a select number of the anionic or cationic charges may be neutralised, for example by end-capping of one or more of the functional group, to moderate the net anionic or cationic charge and thus the complexation of the bioactive molecule. In one embodiment, the dendrimer is lipidated. It will be appreciated that the dendrimer may comprise many different building blocks, such as the compound of the first aspect. In this regard, lipidation can occur on any of the building blocks. For instance, the lipidation can occur on the compound of the first aspect and/or another building block (for example, another amino acid building block).

In another embodiment, the bioactive molecule is bonded to a compound of the first aspect, which is itself within or attached to the macromolecule, for example tethered to an antibody or antibody fragment.

Examples of suitable bioactive molecules are, but are not limited to, genetic material, peptide therapeutics, small molecule drugs, drug conjugates and ionic compounds. The nature of the bioactive molecule is not particularly limited so long as it can be complexed or bonded to the macromolecule, or chemically modified to do so.

The genetic material can be selected from the group consisting of nucleic acid, oligonucleotides, whether sense or antisense oligonucleotides, short interfering RNA (siRNA) and other ss and ds RNA constructs. Nucleic acids can also be in the form of plasmid DNA to thereby facilitate expression of the plasmid-encoded DNA in a host cell.

It is contemplated that bioactive molecules which do not normally comprise an overall, or sufficient, positive or negative charge, if required, can be engineered to comprise sufficient positive or negative charge to complex with the relevant macromolecule.

Thus the fourth aspect provides for vehicles to enable delivery of bioactive molecules for the treatment or prophylaxis of a disease, disorder or condition such as an autoimmune disease, a disease of genetic or non-genetic origin, cancer, diabetes and the like.

As used herein, the terms "treat," "treating," and "treatment" refer to administering a therapy in an amount, manner, or mode effective to improve a condition, symptom, or parameter associated with a disease or disorder.

The term "therapeutically effective amount" as used herein refers to an amount of a bioactive molecule disclosed herein that is sufficient to efficaciously treat a disease or disorder in a subject in need thereof.

A bioreducible linkage can be useful in the delivery of bioactive molecules, such as genetic material, to the intracellular environment of a cell. When the delivery vehicle, for example comprising a dendrimer, is directed to and accesses the internal environment of a cell the endogenous glutathione will reduce any disulfide bonds present in the dendrimeric structure due to the inclusion of the compounds of formula I. As discussed, this results in degradation of the dendrimer or breaking of the bond linking the bioactive molecule to the macromolecule and so the bioactive molecule e.g. the genetic material, being released with a subsequent increase in transfection efficacy.

Further, a bioreducible linkage is useful in the situation where the bioactive molecule can only be bonded and not complexed to the terminal dendrimer functionality or other macromolecule. When the disulfide linkage is cleaved the bioactive will be released with only the small connecting portion still attached to it, for example in the case of a compound of formula XI then the 'tail' remaining on the bioactive molecule would be a small —NH—$(CH_3)_2$—SH group which would be unlikely to interfere with its biological activity.

The delivery vehicle can, if required, further comprise a targeting moiety, which can be a proteinaceous or non-proteinaceous molecule, to assist with site-specific delivery of the bioactive.

The terms "complex", "complexed" or "complexing" when used herein refer to the bioactive molecule being attracted to and held in place by appropriate groups of the macromolecule, such as a peptide structure, dendrimer etc., but not being covalently bound thereto.

In some embodiments, the mammal being treated is a human, livestock, a performance animal or a pet.

In some embodiments, the mammal is a human.

Any suitable route of administration can be employed for providing a patient with the delivery vehicle of the fourth aspect. For example, oral, rectal, parenteral, sublingual, buccal, intravenous, intraarticular, intra-muscular, intra-dermal, subcutaneous, inhalational, intraocular, intraperitoneal, intra-cerebroventricular, transdermal, transmucosal and the like can be employed.

According to a sixth aspect, the invention resides in a tag or probe construct comprising a compound of the first aspect bonded to a tag or probe. In other words, the invention resides in a tag or probe construct produced using a compound of the first aspect bonded to a tag or probe.

The tag or probe may possess certain properties allowing it to be detected and/or quantified, such as fluorescence. In one embodiment, the tag or probe may be a fluorescent resonance energy transfer (FRET) probe. A FRET probe may be useful as a tool for detecting elevated thiol levels and/or redox imbalances and a range of theranostic applications. Compound 22 (shown in FIG. 9), is a FRET probe according to this embodiment of the invention. The experimental section indicates this synthesis and use of a FRET probe coupled with a compound of the first aspect.

A seventh aspect of the invention provides a pharmaceutical composition for the treatment or prophylaxis of a disease, disorder or condition comprising an effective amount of a peptide structure of the third aspect or delivery vehicle of the fourth aspect and a pharmaceutically acceptable carrier, diluent and/or excipient.

Pharmaceutical compositions suitable for administration can be presented in discrete units such as vials, capsules, sachets or tablets each containing a predetermined amount of one or more pharmaceutically active compounds of the invention, as a powder or granules or as a solution or a suspension in an aqueous liquid, a non-aqueous liquid, an oil-in-water emulsion or a water-in-oil emulsion. Such compositions can be prepared by any of the methods of pharmacy but all methods include the step of bringing into association one or more compounds of the first aspect, integrated into the structure of or attached to a macromolecule, with the carrier which constitutes one or more necessary ingredients. In general, the compositions are prepared by uniformly and intimately admixing the agents of the invention with liquid carriers or finely divided solid carriers or both, and then, if necessary, shaping the product in to the desired presentation.

By "pharmaceutically acceptable carrier, diluent and/or excipient" is meant a solid or liquid filler, diluent or encapsulating substance that can be safely used in systemic administration. Depending upon the particular route of administration a variety of carriers, such as those well known in the art, can be used. These carriers or excipients can be selected from the group consisting of sugars, starches, cellulose and its derivates, malt, gelatine, talc, calcium sulphate, vegetable oils, synthetic oils, polyols, alginic acid, phosphate buffered solutions, emulsifiers, isotonic saline, and pyrogen-free water.

The following examples are illustrative and non-limiting, of the products and methods described herein. Suitable modifications and adaptations of the variety of conditions, formulations, and other parameters normally encountered in the field and which are obvious to those skilled in the art in view of this disclosure are within the spirit and scope of the invention.

EXPERIMENTAL

Synthesis of Compounds

Synthesis of Boc-dimethyl Cysteamine (Boc-DMCA; 7)

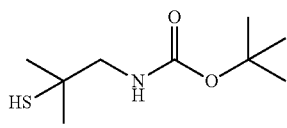

7

Dimethylcysteamine hydrochloride (DMCA HCl) (5 mmol, 0.707 g) was dissolved in water (20 mL) in a reaction flask. A solution of di-tert-butyl dicarbonate (10 mmol, 2.180 g) in $CH_3CN$ (30 mL) was added to the reaction mixture and followed by addition of aqueous $NaHCO_3$ (10 mmol, 0.890 g in 10 mL) solution. The reaction was allowed to stir under an inert ($N_2$) atmosphere at RT for 24 h. The reaction mixture was transferred into a separating funnel and added with an excess of EtOAc (100 mL). The organic phase was collected separately and the remaining aqueous phase washed with EtOAc (2×20 mL). All organic phases were pooled and dried over $MgSO_4$ to remove any residual water. EtOAc was removed in vacuo and the final product was collected as a viscous liquid and vacuum dried overnight to remove any traces of EtOAc. Yield (82%, 0.84 g). TLC: $R_f$ value 0.85 (n-hexane:EtOAc=3:2, UV inactive, stained with $KMnO_4$ produces yellow spot upon drying). HRMS (ESI-TOF): $[M-H]^+$ calculated for $C_9H_{19}NO_2S^-$, 204.1063, found 204.1021; $^1H$ NMR (500 MHz, $CDCl_3$): δ 1.33 (s, 6H, $2CH_3$), 1.44 (s, 9H, $3CH_3$-Boc), 1.62 (s, H, SH), 3.19 (d, J=6.10 Hz, 2H, $CH_2$), 4.98 (s, 1H, NHCO); $^{13}C$ NMR (500 MHz, $CDCl_3$): δ 25.4, 28.5, 48.3, 80.4, 156.1 ppm.

Synthesis of Fmoc-dimethyl Cysteamine (Fmoc-DMCA; 12)

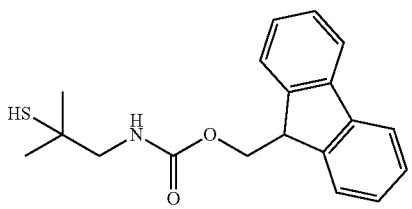

12

DMCA.HCl (5 mmol, 0.707 g) was dissolved in water (20 mL) within a reaction flask. Separately, Fmoc-N-hydroxysuccinimide ester (5 mmol, 1.685 g) was dissolved in $CH_3CN$ (30 mL) and added to the reaction followed by addition of aqueous $NaHCO_3$ (10 mmol, 0.890 g, 10 mL) solution. The reaction was allowed to stir under an inert atmosphere ($N_2$) at RT for 18 h, after which it was transferred into a separating funnel and excess of EtOAc (100 mL) was added. The organic phase was collected and the remaining aqueous phase was washed with EtOAc (2×20 mL). The organic phases were pooled and dried over MgSO4 to remove residual water. EtOAc was removed in vacuo and the resultant white solid product was collected and dried under vacuum. Further, the final yellowish white coloured solid product was purified by column chromatography with solvent mixture of n-hexane and EtOAc (3:2). Yield (67%, 1.09 g). TLC: $R_f$=0.78 (n-hexane:EtOAc=3:2, UV active, illuminates under UV light). HRMS (ESI-TOF): $[M+Na]^+$ calculated for $C_{19}H_{21}NNaO2S+$, 350.1191, found 350.1573. 1 H NMR (500 MHz, $CDCl_3$): δ 1.35 (s, 6H, $2CH_3$), 1.63 (s, H, SH), 3.28 (d, J=6.50 Hz, 2H, $CH_2$), 4.24 (t, J=6.78 Hz 1H, CH-Fmoc), 4.44 (d, J=6.90 Hz, 2H, $CH_2$-Fmoc), 5.23 (s, 1H, NHCO), 7.30-7.33 (td, J=7.46 Hz 2H, Fmoc), 7.40 (t, J=7.46 Hz, 2H, Fmoc), 7.61 (d, J=7.45 Hz, 2H, Fmoc), 7.77 (d, J=7.46 Hz, 2H, Fmoc); $^{13}C$ NMR (500 MHz, $CDCl_3$): δ 29.8, 45.6, 47.4, 54.3, 66.8, 120.1, 125.1, 127.2, 127.8, 141.4, 144.0, 156.7 ppm

Synthesis of Mtt-dimethyl Cysteamine (Mtt-DMCA; 13)

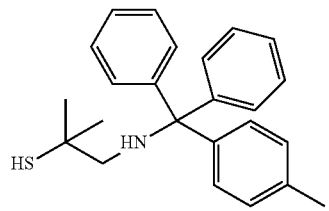

13

DMCA.HCl (5 mmol, 0.707 g) was dissolved in water (20 mL) in a reaction flask. A solution of 4-methyl trityl chloride (Mtt-Cl; 5 mmol, 1.464 g) in $CH_3CN$ (30 mL) was added to the reaction and followed by addition of aqueous $NaHCO_3$ (10 mmol, 0.890 g, 10 mL) solution. The reaction was allowed to stir under an inert ($N_2$) atmosphere for 24 h at RT. The reaction mixture was transferred to a separating funnel to which an excess of EtOAc (100 mL) was added. The organic phase was collected and the remaining aqueous phase was washed with EtOAc (2×50 mL). All organic phases were pooled and dried over $MgSO_4$ to remove any residual water. EtOAc was removed in vacuo and the final product was collected as a clear, viscous liquid. The crude product was purified by column chromatography with n-hexane and EtOAc (3:2) as the solvent mixture. Yield (55%, 0.99 g). TLC: $R_f$ value 0.80 (n-hexane:EtOAc=3:2, UV active, illuminates under UV light). HRMS (ESI-TOF): $[M-H]^+$ calculated for $C_{24}H_{26}NS^-$, 360.1791, found 360.1787. $^1H$ NMR (500 MHz, $CDCl_3$): δ 1.44 (s, 6H, $2CH_3$), 1.69 (s, H, SH), 2.18 (s, 3H, $CH_3$), 2.33 (s, 2H, $CH_2$), 7.12 (d, J=8.10 Hz, 2H, Mtt), 7.20 (t, J=7.35 Hz, 2H, Mtt), 7.29 (t, J=7.90 Hz, 4H, Mtt), 7.42 (d, J=8.25 Hz, 2H, Mtt), 7.54 (d, J=7.40 Hz, 4H, Mtt); $^{13}C$ NMR (500 MHz, $CDCl_3$): 21.1, 31.1, 45.8, 56.9, 70.3, 126.3, 127.4, 128.1, 128.7, 129.4, 135.9, 143.26, 146.4 ppm.

Synthesis of Boc-Cys(S—SC(CH₃)₂CH₂NH(Boc))—OCH₃ (11)

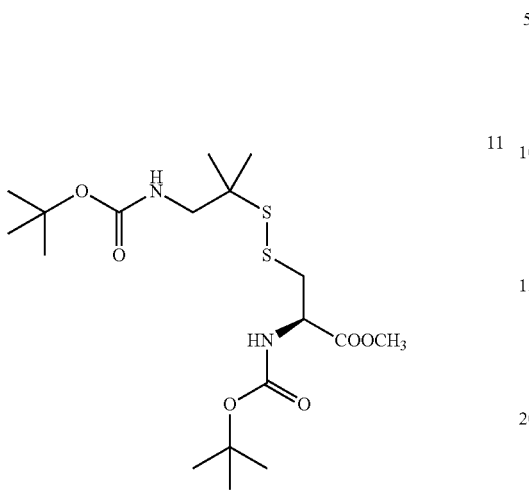

1-Chlorobenzotriazole (BtCl) (1.5 mmol, 0.234 g) and benzotriazole (BtH) (1.0 mmol, 0.278 g) were dissolved in the CH₂Cl₂ (15 mL) in a reaction flask. A solution of Boc-Cys-OCH₃ (1 mmol, 0.237 g) in CH₂Cl₂ (1 mL) was added to the reaction mixture followed by addition of Et₃N (1 mmol, 0.101 g). The reaction was allowed to stir under an inert (N₂) atmosphere for 2 h at −78° C. A solution of Boc-DMCA (1.5 mmol, 0.308 g) in CH₂Cl₂ (1 mL) was added to the reaction mixture which was stirred under an inert (N₂) atmosphere for a further 4 h at −78° C. The reaction was quenched with a mixture of Na₂S₂O₃ (0.500 g in 5 mL water) and saturated NaHCO₃ (5 mL) solution at 0° C. for 30 min. The organic phase was collected and washed with saturated NaCl. The organic phase was dried over MgSO₄ and CH₂Cl₂ removed in vacuo. The crude residue was purified by column chromatography with n-hexane and EtOAc (5 to 30% EtOAc, gradient) as the solvent mixture. Yield (72.18%, 0.315 g). TLC: $R_f$ value 0.48 (n-hexane:EtOAc=3:2, UV inactive, stained with KMnO₄ yellow spot upon drying). HRMS (ESI-TOF): [M+H]⁺ calculated for $C_{18}H_{35}N_2O_6S_2^+$, 439.1937, found 439.1932. ¹H NMR (500 MHz, MeOD): δ 1.25 (s, 6H, 2CH₃), 1.44 (s, 18H, Boc, 6CH₃), 3.11-3.15 (d, J=4.87 Hz, 1H, d, J=4.87 Hz, 1H, CH₂), 3.20 (s 2H, CH₂), 3.73 (s, 3H, ester, 1CH₃), 4.44 (d, J=6.46 Hz, 1H, CH); ¹³C NMR (500 MHz, MeOD): δ 25.6, 28.7, 42.5, 50.1, 52.3, 52.9, 54.5, 80.1, 80.7, 157.6, 158.4, 172.8 ppm.

Synthesis of Boc-Cys(S—SC(CH₃)₂CH₂NH(Boc))—OH (4)

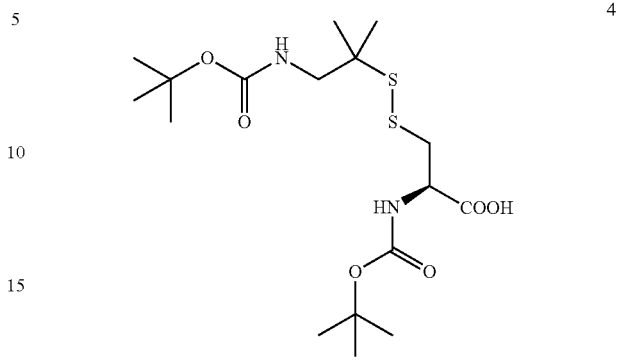

To a stirred solution of Boc-Cys(S—SC(CH₃)₂CH₂NH(Boc))—OCH₃ (0.438 g, 1.0 mmol) in methanol (4 mL) was slowly added a NaOH (0.005 g, 1.3 mmol, 4 mL water) solution, which was then stirred for 2 h at 0° C. The reaction was allowed to stir under an inert (N₂) atmosphere overnight at RT. The reaction mixture was mixed with an excess of EtOAc (50 mL). The organic phase was collected and dried over Na₂SO₄ to remove any residual water. EtOAc was removed in vacuo. The crude product was purified by column chromatography using a chloroform and methanol (95:5) solvent mixture. Yield (85%, 0.360 g). TLC: $R_f$ value 0.52 (chloroform:methanol=4:1, UV inactive, stained with KMnO₄ yellow spot upon drying). HRMS (ESI-TOF): [M−H]⁺ calculated for $C_{17}H_{31}N_2O_6S_2^-$, 423.1629, found 423.1475. ¹H NMR (500 MHz, CDCl₃): δ 1.25 (s, 6H, 2CH₃), 1.45 (s, 18H, Boc, 6CH₃), 3.11-3.20 (dd, J=0.35 Hz, 1H, dd, J=5.20 Hz, 1H, CH₂), 3.23 (s, 2H, CH₂), 4.59 (d, J=5.30 Hz, 1H, CH), 5.10 (s, 1H, NHCO), 5.47 (d, J=6.10 Hz, 1H, NHCO); ¹³C NMR (500 MHz, CDCl₃): δ 25.1, 28.4, 41.7, 48.5, 52.7, 53.4, 79.7, 80.5, 155.4, 156.4, 174.2, 176.7.

Synthesis of Fmoc-Cys(S—SC(CH₃)₂CH₂NH(Fmoc))-OCH₃ (15)

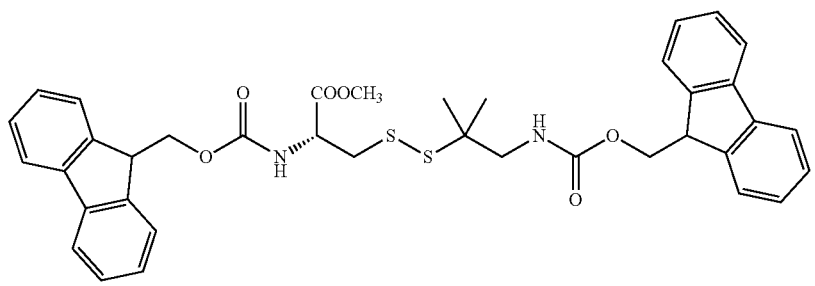

BtCl (1.5 mmol, 0.151 g) and BtH (1.0 mmol, 0.119 g) were dissolved in CH₂Cl₂ (15 mL) in a reaction flask. A solution of Fmoc-Cys-OCH₃ (1.0 mmol, 0.357 g) in CH₂Cl₂ (2 mL) was added dropwise to the reaction mixture and followed by addition of Et₃N (1.0 mmol, 0.101 g). The reaction was allowed to stir under an inert (N₂) environment for 2 h at −78° C. Fmoc-DMCA (1.5 mmol, 0.490 g) in CH₂Cl₂ (1 mL) was added slowly to the reaction mixture. The reaction was stirred under an inert (N₂) environment for 4 h at −78° C. The reaction was then quenched with a mixture of Na₂S₂O₃ (0.200 g in 5 mL water) and saturated NaHCO₃ (5 mL) solution at 0° C. for 30 min. The organic phase was collected and washed with saturated NaCl. The organic phase was dried over MgSO₄ and CH₂Cl₂ removed in vacuo. The crude residue was purified by chromatography with n-hexane and EtOAc (5 to 30% EtOAc, gradient) as the solvent mixture. Yield (58.35%, 0.398 g). TLC: $R_f$ value 0.42 (n-hexane:EtOAc=3:2, UV active, illuminates under UV light). HRMS (ESI-TOF): [M+H]⁺ calculated for $C_{38}H_{39}N_2O_6S_2^+$, 683.2244, found 683.2298. ¹H NMR (500 MHz, CDCl₃): δ 1.25 (s, 6H, 2CH₃), 3.12-3.24 (dd, J=4.95 Hz, 1H, dd, J=4.55 Hz, 1H, CH₂), 3.30 (s 1H, 2CH₂), 3.75 (s, 3H, ester, CH₃), 4.15 (s, 1H, CH-Fmoc) 4.24 (s, 1H, CH-Fmoc), 4.40 (d, J=7.46 Hz, 4H, 2CH₂, Fmoc), 4.71 (d, J=7.75, 1H, CH), 5.31 (s, 1H, NHCO), 5.75 (d, 1H, J=7.75 Hz, NHCO), 7.28-7.31 (m, 4H, Fmoc), 7.39 (t, J=7.46 Hz, 4H, Fmoc), 7.56-7.62 (m, 4H, Fmoc), 7.76 (dd, J=7.38 Hz, 4H, Fmoc); ¹³C NMR (500 MHz, CDCl₃): δ 25.1, 41.4, 47.4, 48.9, 51.6, 53.0, 53.7, 66.7, 67.5, 120.0, 125.2, 127.2, 127.9, 141.4, 144.0, 155.8, 156.8, 170.9 ppm.

Synthesis of Fmoc-Cys(S—SC(CH₃)₂CH₂NH(Fmoc))—OH (16)

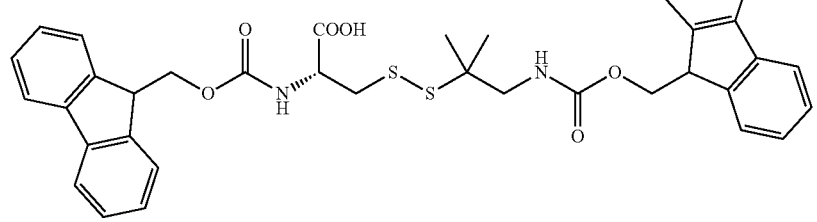

Fmoc-Cys(S—SC(CH₃)₂CH₂NH(Fmoc))—OCH₃ (0.682 g, 1.0 mmol) was dissolved in iPr-OH (14 mL) in a reaction flask. A solution of CaCl₂ (1 M, 6 mL) was added followed by addition of NaOH (0.005 g, 1.3 mmol, 1 mL) solution. The reaction was stirred under an inert (N₂) atmosphere for 18 h at RT. iPr-OH was removed in vacuo and to the remaining aqueous phase was added an excess of EtOAc (50 mL). The organic phase was collected and again aqueous phase was washed with EtOAc (2×20 mL). The pooled organic phase was dried over Na₂SO₄ and EtOAc was removed in vacuo. The residue was purified by column chromatography with chloroform and methanol (95:5) as the solvent mixture. Yield (71%, 0.470 g). TLC: $R_f$ value 0.51 (chloroform:methanol=4:1, UV active, illuminates under UV light). HRMS (ESI-TOF): [M−H]⁺ calculated for $C_{37}H_{36}N_2O_6S_2^-$, 667.1937, found 667.1939. ¹H NMR (500 MHz, CDCl₃): δ 1.25 (s, 6H, 2CH₃), 2.88-3.16 (dd, J=8.70 Hz, dd, J=6.90 Hz, 2H, CH₂) 3.30 (d, J=6.00 Hz, 2H, 1CH₂), 4.24 (t, J=7.13 Hz, 2H, CH-Fmoc), 4.41 (d, J=7.33 Hz, 4H, CH₂-Fmoc), 4.74 (d, 1H, t-C, CH), 5.29 (s, NHCO), 5.78 (d, J=6.75 Hz, NHCO), 7.27-7.39 (m, 8H, Fmoc), 7.54-7.59 (m, 4H, Fmoc), 7.74 (d, J=7.18 Hz, 4H, Fmoc); ¹³C NMR (500 MHz, CDCl₃): δ 25.1, 41.4, 47.4, 48.9, 52.9, 53.7 66.7, 67.4, 120.0, 125.1, 127.1, 127.8, 141.4, 143.9, 155.7, 156.7, 170.8 ppm.

Synthesis of Fmoc-Cys(S—SC(CH₃)₂CH₂NH(Boc))—OCH₃ (17)

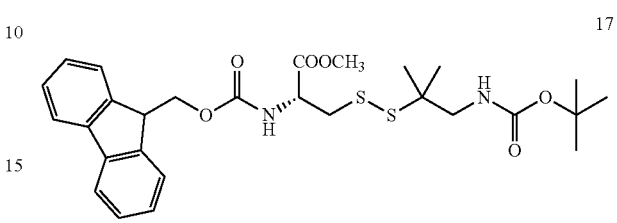

BtCl (0.75 mmol, 0.115 g) and BtH (0.5 mmol, 0.060 g) were dissolved in CH₂Cl₂ (15 mL) in a reaction flask. A solution of Fmoc-Cys-OCH₃ (0.5 mmol, 0.178 g) in CH₂Cl₂ (2 mL) was added dropwise to the reaction mixture followed by addition of Et₃N (0.75 mmol, 0.075 g). The reaction was stirred under an inert (N₂) environment for 2 h at −78° C. A solution of Boc-DMCA (0.75 mmol, 0.153 g) in CH₂Cl₂ (1 mL) was added slowly and the reaction was stirred under an inert (N₂) environment for 4 h at −78° C. The reaction was quenched with a mixture of Na₂S₂O₃ (0.200 g in 5 mL water) and saturated NaHCO₃ (10 mL) solution at 0° C. for 30 min. The organic phase was collected and washed with saturated NaCl. The organic phase was dried over MgSO₄ and CH₂Cl₂ was removed in vacuo. The crude residue was purified by column chromatography with n-hexane and EtOAc (5 to 30% EtOAc, gradient) as the solvent mixture. Yield (70.50%, 0.205 g). TLC: $R_f$ value 0.43 (n-hexane:EtOAc=3:2, UV active, illuminates under UV light). HRMS (ESI-TOF): [M+Na]⁺ calculated for $C_{28}H_{36}N_2NaO_6S_2^+$, 583.1912, found 583.2285. ¹H NMR (500 MHz, CDCl₃): δ 1.25 (s, 6H, 2CH₃), 1.41 (s, 9H, Boc, 6CH₃), 3.11-3.15 (dd, J=5.25 Hz, 2H, CH₂), 3.19-3.33 (dd, J=6.00, Hz, 2H, CH₂), 3.80 (s, 3H, ester, CH₃), 4.39 (d, J=7.00 Hz, 1H, CH-Fmoc), 4.69 (d, J=7.20 Hz, 2H, CH₂-Fmoc), 4.96 (s, NHCO), 5.75 (d, J=7.45, NHCO), 7.29-7.32 (t, J=7.45 Hz, 2H, Fmoc), 7.38-7.41 (t, J=7.35 Hz, 2H, Fmoc), 7.60-7.62 (t, J=6.15 Hz, 2H, Fmoc), 7.76 (d, J=7.55 Hz, 2H, Fmoc); ¹³C NMR (500 MHz, CDCl₃): δ 25.2, 28.4, 47.2, 48.4, 51.8, 52.9, 53.7, 65.9, 67.5, 79.5, 120.1, 125.3, 127.2, 127.9, 128.1, 141.4, 143.9, 155.7, 156.2, 170.8 ppm.

Synthesis of Fmoc-Cys(S—SC(CH₃)₂CH₂NH(Boc))—OH; (18)

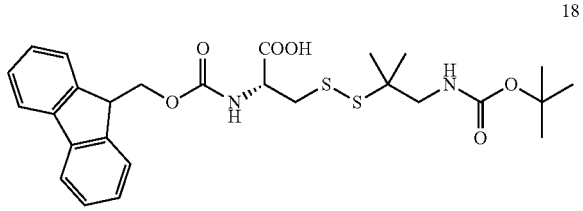 [SMILES: CC(C)(C)OC(=O)NCC(C)(C)SSC[C@H](NC(=O)OCC1c2ccccc2-c2ccccc21)C(=O)O]

Fmoc-Cys(S—SC(CH₃)₂CH₂NH(Boc))—OCH₃ (0.560 g, 1.0 mmol) was dissolved in iPr-OH (14 mL) in a reaction flask. A solution of CaCl₂ (1 M, 6 mL) solution was added to the reaction mixture followed by addition of NaOH (0.005 g, 1.3 mmol, 1 mL) solution. The reaction was stirred under an inert (N₂) atmosphere for 18 h at RT by monitoring with TLC. iPr-OH was removed in vacuo. To the aqueous phase was added an excess of EtOAc (100 mL). The organic phase was collected and the remaining aqueous phase again washed with EtOAc (2×20 mL). The pooled organic phase was dried over MgSO₄ and EtOAc was removed in vacuo. The residue was purified by column chromatography with chloroform and methanol (95:5) as the solvent mixture. Yield (77%, 0.419 g). TLC: R$_f$ value 0.57 (chloroform:methanol=4:1, UV active, illuminates under UV light. HRMS (ESI-TOF): [M−H]⁺ calculated for, C₂₇H₃₃N₂O₆S₂⁻, 545.1785, found 545.1618. ¹H NMR (500 MHz, CDCl₃): δ 1.25 (s, 6H, 2CH₃), 1.41 (s, 9H, 6CH₃, Boc), 3.11-3.24 (dd, J=9.01 Hz, 2H, dd, J=8.19 Hz, 2H, 2CH₂), 4.24 (t, J=7.81 Hz, 1H, CH-Fmoc), 4.39 (d, J=7.00 Hz, 2H, CH₂, Fmoc), 4.69 (d, J=7.50 Hz, 1H, t-C, CH), 4.95 (s, 1H, NHCO), 5.72 (d, J=7.60 Hz, 1H, NHCO), 7.32 (t, J=7.42 Hz, 2H, Fmoc), 7.40 (t, J=7.45 Hz, 2H, Fmoc), 7.61 (t, J=6.35 Hz, 2H, Fmoc), 7.76 (d, J=7.55 Hz, 2H, Fmoc); ¹³C NMR (500 MHz, CDCl₃): δ 25.2, 28.4, 41.8, 47.2, 48.4, 52.9, 53.7, 65.9, 67.5, 79.5, 120.1, 125.3, 127.2, 127.9, 141.4, 143.8, 155.7, 156.2 170.8 ppm.

Synthesis of Fmoc-Cys(S—SC(CH₃)₂CH₂NH(Mtt))—OCH₃ (19)

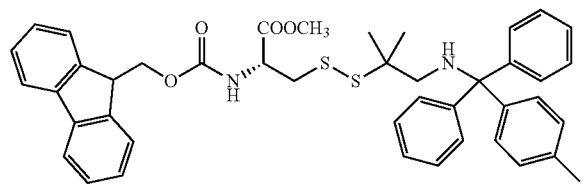

Method (A): BtCl (0.75 mmol, 0.115 g) and BtH (0.5 mmol, 0.060 g) were dissolved in CH₂Cl₂ (15 mL). A solution of Fmoc-Cys-OCH₃ (0.5 mmol, 0.178 g) in CH₂Cl₂ (1 mL) was added dropwise to the reaction mixture. The reaction was stirred under an inert (N₂) environment for 2 h at −78° C. After 1 h, Et₃N (0.75 mmol, 0.075 g) was added to the reaction mixture. After 2 h, a solution of Mtt-DMCA (0.75 mmol, 0.270 g) in CH₂Cl₂ (1 mL) was added slowly to the reaction mixture. The reaction was stirred under an inert (N₂) environment for another 4 h at −78° C. The reaction was quenched with a mixture of Na₂S₂O₃ (0.200 g in 5 mL water) and saturated NaHCO₃ (5 mL) solution at 0° C. for 30 min. The organic phase was collected and washed with saturated NaCl. The pooled organic phase was dried over MgSO₄ and CH₂Cl₂ was removed in vacuo. The crude residue was purified by column chromatography with n-hexane and EtOAc (5 to 30% EtOAc, gradient) as the solvent mixture. Yield (55%, 0.197 g).

Method (B): Fmoc-Cys(S—SC(CH₃)₂NH(Boc))—OCH₃ (0.056 g, 0.1 mmol) was dissolved in CH₂Cl₂ (5 mL) in a reaction flask. TFA (5 mL) was slowly added to the reaction mixture and the reaction was stirred under an inert (N₂) atmosphere for 1 h at RT. CH₂Cl₂ and TFA were removed in vacuo. The residue was re-dissolved in CH₂Cl₂ (10 mL) and a solution of Et₃N (0.020 g, 0.2 mmol) and Mtt-Cl (0.12 mmol, 0.036 g) in CH₂Cl₂ (2 mL) was added. The reaction was stirred under an inert (N₂) atmosphere for 24 h at RT. CH₂Cl₂ and Et₃N were removed in vacuo. The residue was purified by column chromatography with n-hexane and EtOAc (4:1) as the solvent mixture. Yield (69%, 0.0493 g). TLC: R$_f$ value 0.51 (n-hexane:EtOAc=3:2, UV active, illuminates under UV light). HRMS (ESI-TOF): [M−H]⁺ calculated for, C₄₃H₄₄N₂O₄S₂⁻ 715.2664, found 715.2805. ¹H NMR (500 MHz, CDCl₃): δ 1.37 (s, 6H, 2CH₃), 2.20 (s, 2H, CH₂), 2.28 (s, 3H, Mtt-CH₃) 2.64-2.76 (dd, J=4.90 Hz, 1H, dd, J=8.97 Hz, 1H, CH₂), 3.71 (s, 3H, ester, 1CH₃), 4.22 (t, J=7.73 Hz, 1H, CH-Fmoc), 4.34 (t, J=4.78 Hz, 2H, CH₂, Fmoc), 4.45 (m, 1H, CH), 4.53 (s, 1H, NHCO), 5.57 (s, 1H, NHCO), 7.06 (d, J=8.10 Hz, 2H, Mtt), 7.16 (t, J=15.85, 2H, Mtt), 7.23-7.48 (m, 4H, Fmoc; 10H, Mtt), 7.59 (d, J=5.60 Hz, 2H, Fmoc), 7.77 (dd, 2H, Fmoc); ¹³C NMR (500 MHz, CDCl₃): δ 21.0, 26.5, 41.9, 47.2, 51.4, 52.4, 52.7, 53.6, 67.4, 70.2, 120.1, 125.3, 126.4, 127.2, 127.4, 127.9, 128.0, 128.6, 128.6, 128.7, 135.9, 141.4, 143.0, 146.1, 170.8.

Synthesis of Fmoc-Cys(S—SC(CH₃)₂CH₂NH(Mtt))—OH (20)

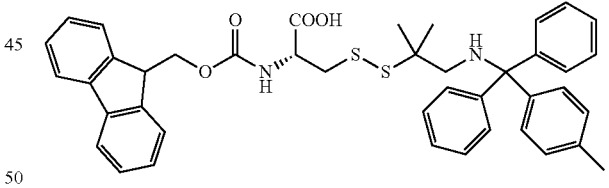

Fmoc-Cys(S—SC(CH₃)₂CH₂NH(Mtt))—OCH₃ (1.0 mmol, 0.715 g) was dissolved in iPr-OH (14 mL) in a reaction flask. A solution of CaCl₂ (1 M, 6 mL) was added to the reaction mixture and followed by addition of an aqueous NaOH (0.005 g, 1.3 mmol, 1 mL) solution. The reaction was stirred under an inert (N₂) atmosphere for 18 h at RT. iPr-OH was removed in vacuo. To the aqueous phase of the reaction mixture was added an excess of EtOAc (100 mL). The organic phase was collected and the aqueous phase washed with (2×20 mL) EtOAc. The pooled organic phase was dried over MgSO₄ to remove any residual water. EtOAc was removed by in vacuo to collect the crude product and further purified by column chromatography with chloroform and methanol (95:5) as the solvent mixture. Yield (70%, 0.489 g). TLC: R$_f$ value 0.52 (n-hexane:EtOAc=4:1, UV active, illuminates under UV light). HRMS (ESI-TOF):

[M–H]⁺ calculated for, $C_{42}H_{41}N_2O_4S_2^-$, 701.2513, found 701.2505. ¹H NMR (500 MHz, CDCl₃): δ 1.40 (s, 6H, 2CH₃), 2.35 (s, 3H, CH₃-Mtt), 2.75, 2.87 (m, 4H, 2CH₂), 4.21 (t, J=7.13 Hz, 1H, CH-Fmoc), 4.24 (tt, J=4.38 Hz, 2H, CH₂, Fmoc), 4.45 (m, 1H, t-C, CH, Cysteine), 5.61 (s, NHCO, Cysteine), 7.05 (d, J=8.11 Hz, 2H Mtt), 7.17 (m, 4H, Mtt), 7.30 (t, J=7.25, 2H, Mtt), 7.32-7.35 (m, 2H, 2H, Mtt), 7.36 (m, 2H, Fmoc), 7.40 (m, 2H, Fmoc), 7.46 (d, J=8.67 Hz, 4H, Mtt), 7.56 (t, J=5.10 Hz, 2H, Fmoc), 7.74 (m, 2H, Fmoc); ¹³C NMR (500 MHz, CDCl₃): δ 21.0, 26.5, 41.9, 47.2, 52.4, 52.7, 53.6, 67.3, 70.2, 120.1, 125.3, 126.3, 127.23, 127.8, 128.6, 128.6, 128.7, 128.7, 135.3, 141.4, 143.8, 146.1, 146.2, 170.8.

Synthesis of Boc-Cys(S— SC(CH₃)₂CH₂NH (Boc))—OCH₃ (10)

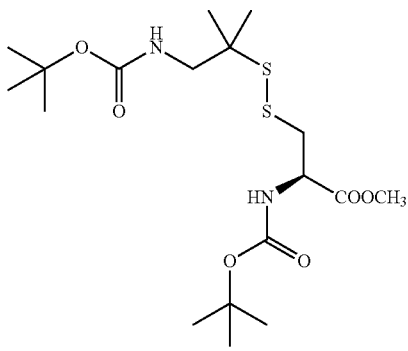

Boc-Cys-OCH₃ (1.0 mmol, 0.237 g) was dissolved in CH₂Cl₂ (10 mL) in a reaction flask. Boc-DMCA (1.0 mmol, 0.205 g) in CH₂Cl₂ (5 mL) and Et₃N (1.0 mmol, 0.101 g) were added to the reaction mixture. The reaction was allowed to stir under an inert (N₂) environment for 24 h at RT. CH₂Cl₂ and Et₃N were removed in vacuo. The crude residue was purified by column chromatography with n-hexane and EtOAc (5 to 30% EtOAc, gradient) as the solvent mixture. Yield (15%, 0.065 g).

Synthesis of Fmoc-Cys(S—SC(CH₃)₂CH₂NH (Fmoc))—OCH₃ (15)

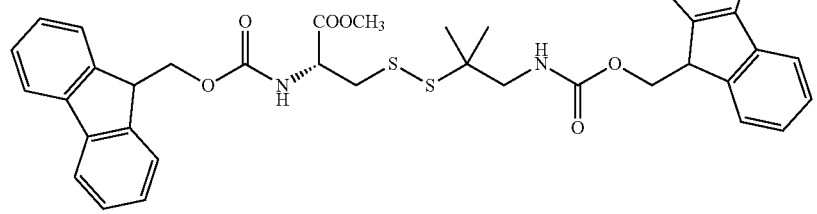

Fmoc-Cys-OCH₃ (1.0 mmol, 0.357 g) was dissolved in CH₂Cl₂ (10 mL). A solution of Fmoc-DMCA (1.0 mmol, 0.327 g) in CH₂Cl₂ (5 mL) and Et₃N (1.0 mmol, 0.10 g) were added to the reaction mixture. The reaction was stirred under an inert (N₂) environment for 24 h at RT. CH₂Cl₂ and Et₃N were removed in vacuo. The crude residue was purified by column chromatography using n-hexane and EtOAc (5 to 30% EtOAc, gradient) as the solvent mixture. Yield (40%, 0.273 g).

Synthesis of Fmoc-Cys(S—SC(CH₃)₂CH₂NH (Boc))—OCH₃ (17)

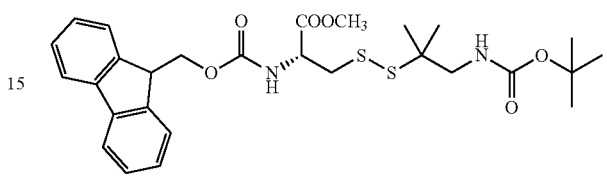

Fmoc-Cys-OCH₃ (1.0 mmol, 0.357 g) was dissolved in CH₂Cl₂ (10 mL) in a reaction flask. A solution of Boc-DMCA (1.0 mmol, 0.205 g) in CH₂Cl₂ (5 mL) and Et₃N (1.0 mmol, 0.101 g) were added to the reaction mixture. The reaction was stirred under an inert (N₂) environment for 24 h at RT. CH₂Cl₂ and Et₃N were removed in vacuo. The crude residue was purified by column chromatography with n-hexane and EtOAc (5 to 30% EtOAc, gradient) as the solvent mixture. Yield (52%, 0.302 g).

Synthesis of Fmoc-Cys(S—SC(CH₃)₂CH₂NH (Mtt))—OCH₃ (19)

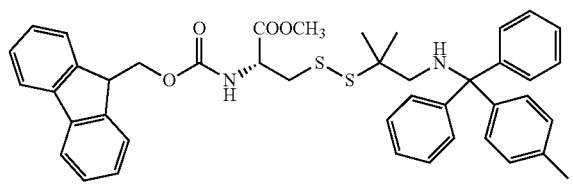

Fmoc-Cys-OCH₃ (1.0 mmol, 0.357 g) was dissolved in CH₂Cl₂ (10 mL) in a reaction flask. A solution of Mtt-DMCA (1.0 mmol, 0.361 g) in CH₂Cl₂ (5 mL) and Et₃N (1.0 mmol, 0.101 g) were added to the reaction mixture. The reaction was stirred under an inert (N₂) environment for 24 h at RT. CH₂Cl₂ and Et₃N were removed in vacuo. The crude residue was purified by column chromatography with n-hexane and EtOAc (5 to 30% EtOAc, gradient) as the solvent mixture. Yield (42%, 0.300 g).

Evaluation of Compound Stability to Reagents Applied to SPPS

Prior to exploring further applications of the novel disulfide-bridged amino acid, the stability of its —S—S— bond to reagents/conditions employed during Fmoc-SPPS had to be established. For each deprotection step performed during peptide synthesis, a resin bound random amino acid is exposed to basic reagents with 20% v/v piperidine in DMF. —S—S— bond stability to these basic conditions was therefore trialled using a di-Boc protected disulfide bridged amino acid of the invention (compound 11), since the Boc protecting groups themselves would be stable to the basic conditions. A 5,5'-dithiobis-(2-nitrobenzoic acid) (DTNB) assay was used to assess stability of the S—S bond after being subjected to the aforementioned basic conditions. This assay was developed to enable rapid and convenient colorimetric measurement of free thiols generated in the reaction mixture. Premature reduction of the disulfide-containing amino acid by piperidine would lead to the formation of free thiols that react with DTNB releasing $NTB^{2-}$, which can be readily identified spectrophotometrically at 412 nm.

Sample Preparation—DTNB Stock Solution

DTNB (1 mg) was dissolved in 1 mL of methanol and a 1 mg/mL stock solution was prepared. A DTNB calibration curve was prepared by measurement of the absorbance ($\lambda_{max}$=308 nm) over a range of concentrations (5, 10, 15, 20, and 25 µg/mL) in the presence of 20% v/v piperidine in DMF (100 µL).

Reaction of Thiol from Boc-Cys-OCH$_3$ with 20% v/v Piperidine in DMF

Boc-Cys-OCH$_3$ (compound 8, 1 mg) was weighed and dissolved in 1 mL of methanol to prepare 1 mg/mL stock solution, with different concentrations of thiol-containing samples (1.25, 2.5, 5, 10, 12.5 µg/mL) being prepared from the stock solution. To each concentration of thiol-containing sample was added 20% piperidine in DMF (100 µL) followed by DTNB (final concentration 10 µg/mL). Next the absorbance of each mixture was recorded to determine the presence of both DTNB ($\lambda_{max}$=308 nm) and $NTB^{2-}$ ($\lambda_{max}$=412 nm). Final concentrations of 20% piperidine in DMF and DTNB were identical in the DTNB, thiol-containing, and sample solutions.

Reaction of Disulfide-Bridged Amino Acid with 20% v/v Piperidine in DMF

Boc-Cys(S—SC(CH$_3$)$_2$CH$_2$NH(Boc)-OCH$_3$ (compound 11, 1 mg) was incubated in 20% v/v piperidine in DMF (1 mL) for 6 h. Different concentrations of compound 11 (5, 10, 15, 20, 25 µg/mL) samples were then prepared and added to DTNB (final concentration 10 µg/mL in solution). After 30 min the absorbance was recorded for both DTNB ($\lambda_{max}$=308 nm) and $NTB^{2-}$ ($\lambda_{max}$=412 nm).

DTNB Assay

Figure 5:
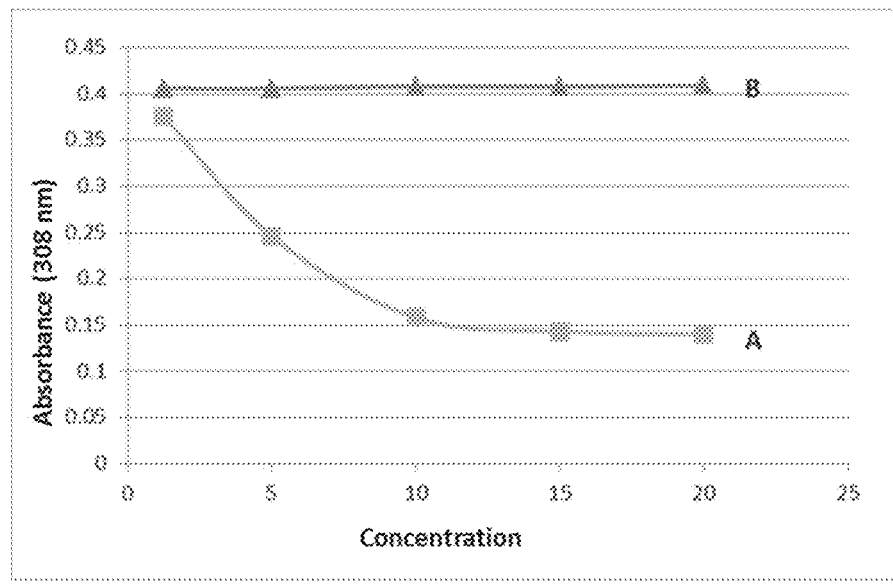
FIG. 5 is a graphical representation of the absorbance at 308 nm (A) with increasing Boc-cysteine methyl ester concentration; and (B) with increasing compound 11 concentration.
Figure 6:
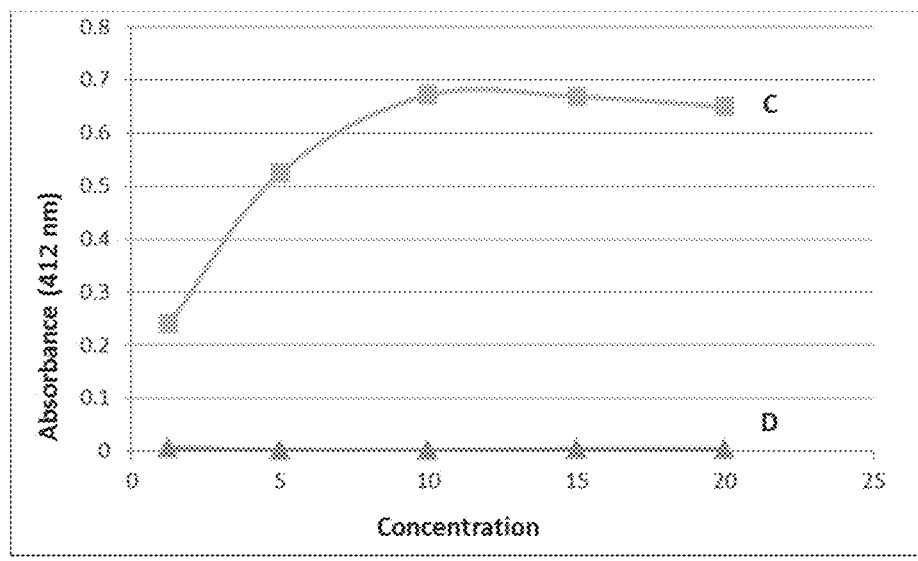
FIG. 6 is a graphical representation of the absorbance at 412 nm (C) with increasing Boc-cysteine methyl ester concentration; and (D) with increasing compound 11 concentration.

The colorimetric reagent DTNB ($\lambda_{max}$=308 nm) was serially diluted in methanol (1 mg-10 µg/mL, with the absorbance of each sample recorded and plotted against the respective DTNB concentration. In presence of free thiols, DTNB is readily reduced to $NTB^{2-}$ and an absorbance shift from 308 nm to 412 nm is detected spectrophotometrically. Boc-Cys-OCH$_3$ was employed as the source of thiols and following reaction with DTNB at various concentrations, absorbance readings at 308 & 412 nm were recorded. As expected, with an increasing concentration of thiol, a reduction in absorbance intensity at 308 nm, with a corresponding increase at 412 nm was observed (FIGS. 5 and 6).

Stability of the disulfide-bridged amino acid (compound 11) to basic conditions was assessed next, where it was first incubated with 20% v/v piperidine in DMF for up to 6 h and from that different concentrations of samples were prepared. These 20% v/v piperidine in DMF exposed samples were mixed with DTNB. The absorbance of each DTNB-containing sample was measured at both 308 & 412 nm to monitor for loss of absorbance at 308 nm, and a corresponding increase at 412 nm.

The results confirm that increasing stability of disulfide bonds to both basic and reductive conditions can be achieved simultaneously by introducing steric bulk e.g. in this example via gem-methyl groups on the carbon immediately adjacent to the disulfide bond. In this work, base stability of this steric stabilised disulfide bond was confirmed paving the way for its application across Fmoc- and Boc-solid phase chemistries. Base stability of the novel disulfide-bridged amino acid was confirmed in 20% v/v piperidine in DMF for 6 h, using the DTNB assay, as no free thiols were generated/detected from reaction of the amino acid with piperidine. This would have been expected if the —S—S— bond was unstable to basic pH conditions.

Application of Disulfide-Bond Containing Amino Acids—Bioreducible Dendrimers, Cyclic Peptides and FRET Probe-Based Systems General protocol for peptide dendrimer synthesis:

1. Rink amide resin (typically 0.79 mmol, mass based on original resin loading) was weighed in a clean, dry SPPS glass vessel and swelled in DMF (2 h) with gentle agitation.
2. To remove the Fmoc protecting group from the resin, DMF was then vacuum drained and 20% v/v piperidine in DMF was added to a volume that fully submerged the resin; this was followed by gentle agitation for 8 min. The resin mixture was then drained and incubated for a second time in 20% v/v piperidine in DMF for a further 8 min.
3. The resin was thoroughly washed with DMF (2-3 resin volumes) then drained under vacuum.
4. Amino acid coupling to the resin: Fmoc-AA-OH where 'AA' represents a standard amino acid or a particular disulfide bond containing amino acid of the first aspect employed (3 eq relative to resin loading) was activated with 0.5 M N,N,N',N'-Tetramethyl-O—(1H-benzotriazol-1-yl)uronium hexafluorophosphate (HBTU) (3 eq) and N,N-diisopropylethylamine (DIPEA) (3 eq). All amino acids and coupling reagents were used in 3 eq w.r.t original resin loading unless otherwise stated, and the mixture was gently agitated for 30-45 min.
5. A Ninhydrin test was performed to verify the completeness of the reaction. Ninhydrin value (NV) and coupling efficiency (%) were calculated from equations 1 and 2 below. Coupling was considered complete when the coupling efficiency was ≥99.6%, after which the resin was washed thoroughly (2-3 resin volumes) with DMF. The ninhydrin test procedure as follows: A small amount of resin was collected into a sintered filter funnel and washed with DMF followed by acetone and the resin was then dried for 2 min under vacuum. Approximately 1-2 mg of resin was weighed out and collected in a test tube for the ninhydrin test. To this was added with 2 drops of Reagent 1 (~50 µL, 76% w/w phenol in ethanol), 4 drops of Reagent 2 (~100 µL, 0.2 mM potassium cyanide in pyridine) and 2 drops of Reagent 3 (~50 µL, 0.28 M Ninhydrin in ethanol). Another test without resin beads was performed as a blank reference. Sample and reference test tubes were placed in a preheated heating block at 100° C. for 5 min. Test tubes were removed from the heating block and quickly added to 2.8 mL of 60% ethanol (aq). The absorbance of the resin containing sample solution and blank solution was measured at 570 nm. The ninhydrin value was obtained by using the following formula:

Ninhydrin value (NV)=[($A570 \times V$ mL)/($\epsilon 570 \times W$ mg)]×106    (equation 1), where the extinction coefficient ($\epsilon 570$) is the molar absorbance of free amine groups (1.5×104 M−1 cm-1); A570 is the absorbance reading at 570 nm; W is the mass of the resin in mg; and V is the volume of the sample. The coupling efficiency was calculated in % as follows:

% coupling efficiency=[1−(NV/Substituted value)]×100    (equation 2), where the Substituted value (SV) is expressed in µmol/g; the SV values for the subsequent couplings were calculated as follows:

SV1=[SV/(1+(SV×10−3×Molecular weight of first amino acid))]×103    (equation 3);

and the molecular weight of the first amino acid is calculated by first subtracting 18 amu i.e. molecular weight of H2O that is liberated at each amino acid coupling step.

6. Fmoc-deprotection: Repeat step 2.
7. Repeat steps 3 and 4 of sequential washing and coupling and step 2 of Fmoc deprotection of the amino acids until the desired peptide dendrimer is obtained.
8. After deprotection of the final Fmoc-protecting group and thorough washing with DMF the resin was drained, washed with DCM (2-3 resin volumes) and dried in vacuo.
9. The dried resin was transferred to a 50 mL round-bottomed flask and cleavage reagent mixture added (TFA/DCM/TIPS/H₂O/DCM—90:5:2.5:2.5; 10 mL), with vigorous stirring for 3-4 h at RT.
10. The resin mixture was then vacuum filtered and the filtrate evaporated in vacuo, followed by azeotroping with toluene (3×15 mL) to remove residual TFA.
11. The resulting sticky (off-white) residue was triturated with ice cold diethyl ether (5×10 mL) and then dissolved in water and lyophilized. Crude product after lyophilisation was purified by preparative RP-HPLC and analysed by HR-MS and analytical RP-HPLC.

Synthesis of Asymmetric Peptide Dendrimers

Figure 13:
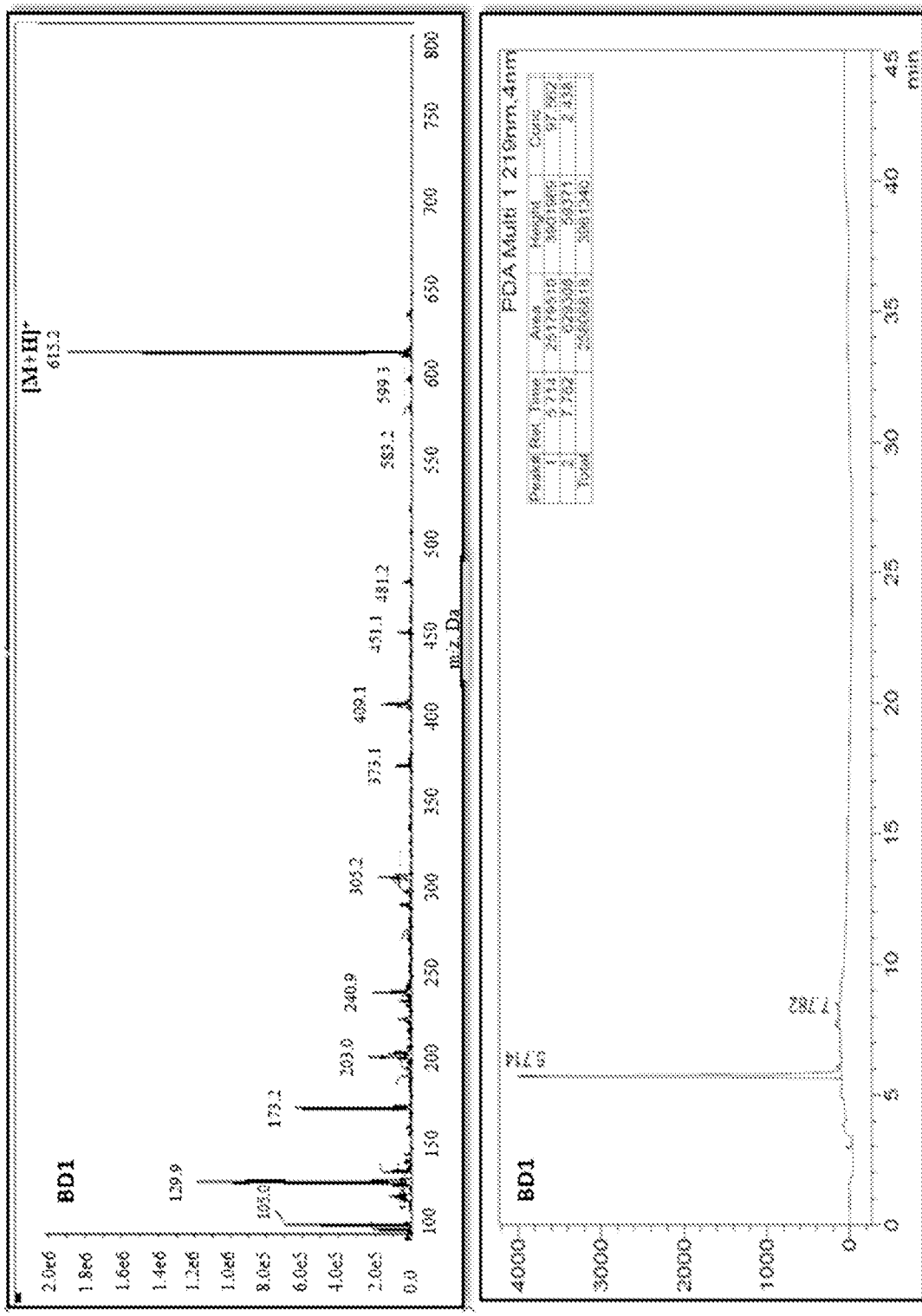
FIG. 13 shows mass spectrometry and HPLC traces for bioreducible dendrimer BD1.
Figure 14:
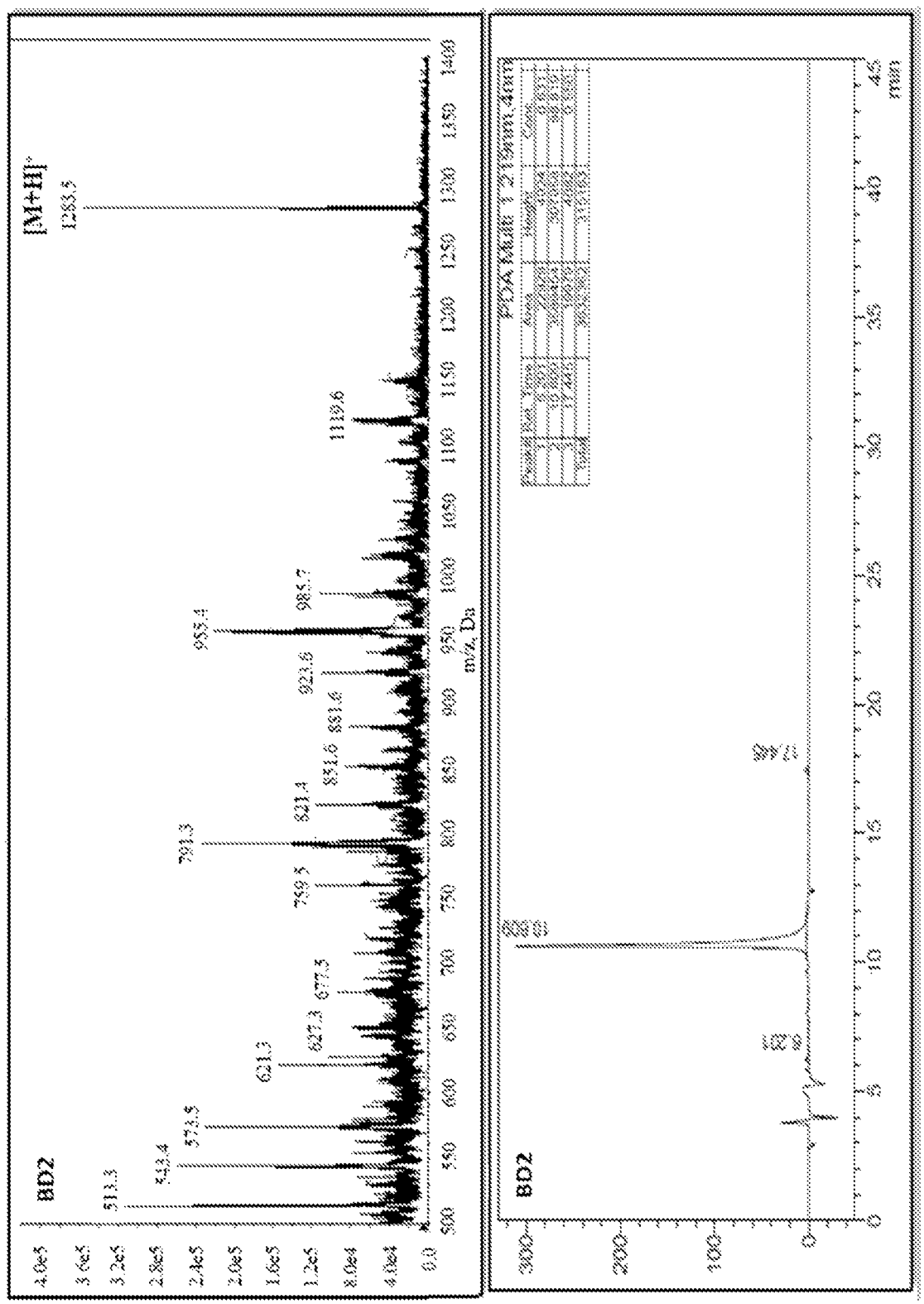
FIG. 14 shows mass spectrometry and HPLC traces for bioreducible dendrimer BD2.
Figure 15:
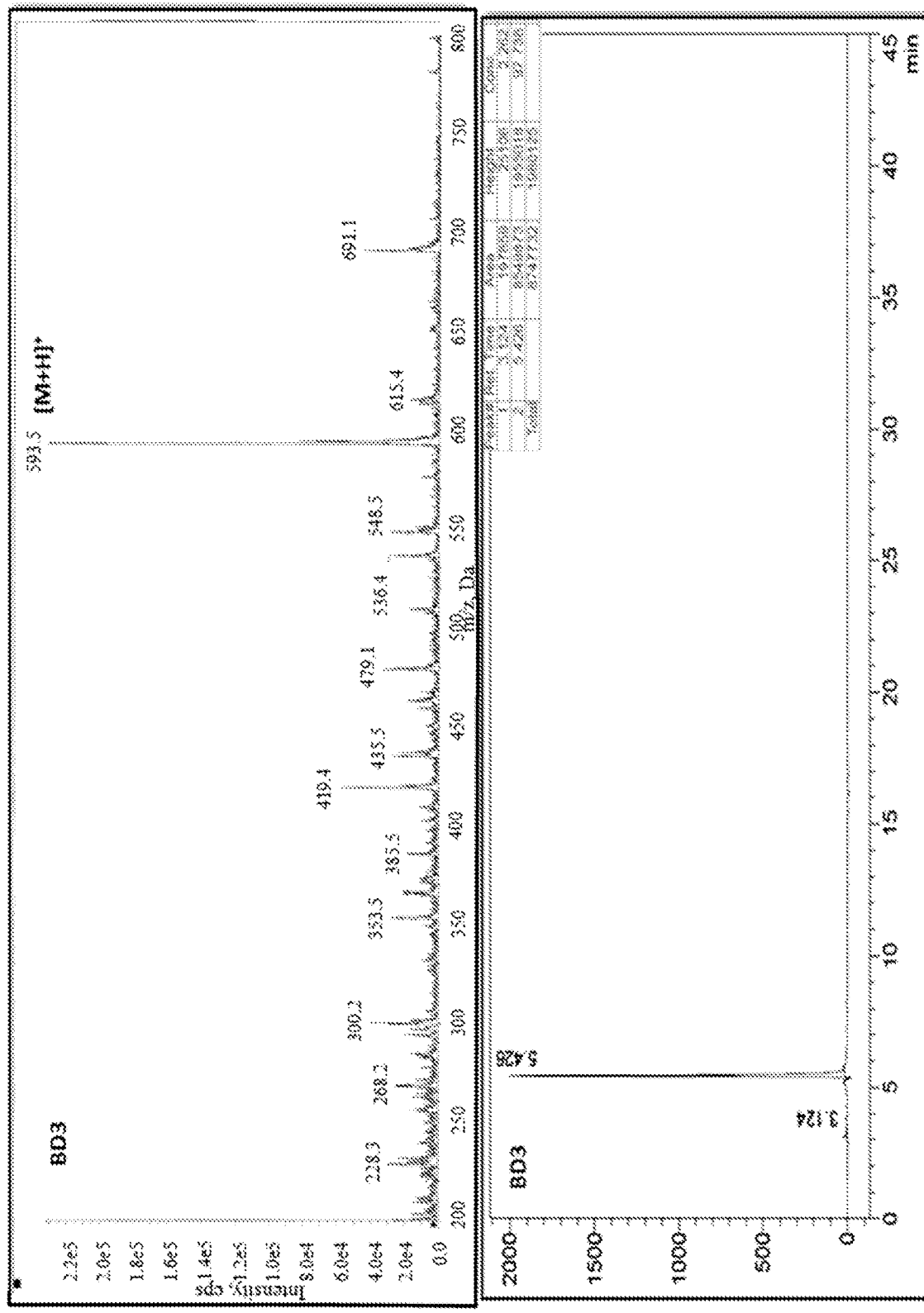
FIG. 15 shows mass spectrometry and HPLC traces for bioreducible dendrimer BD3.
Figure 16:
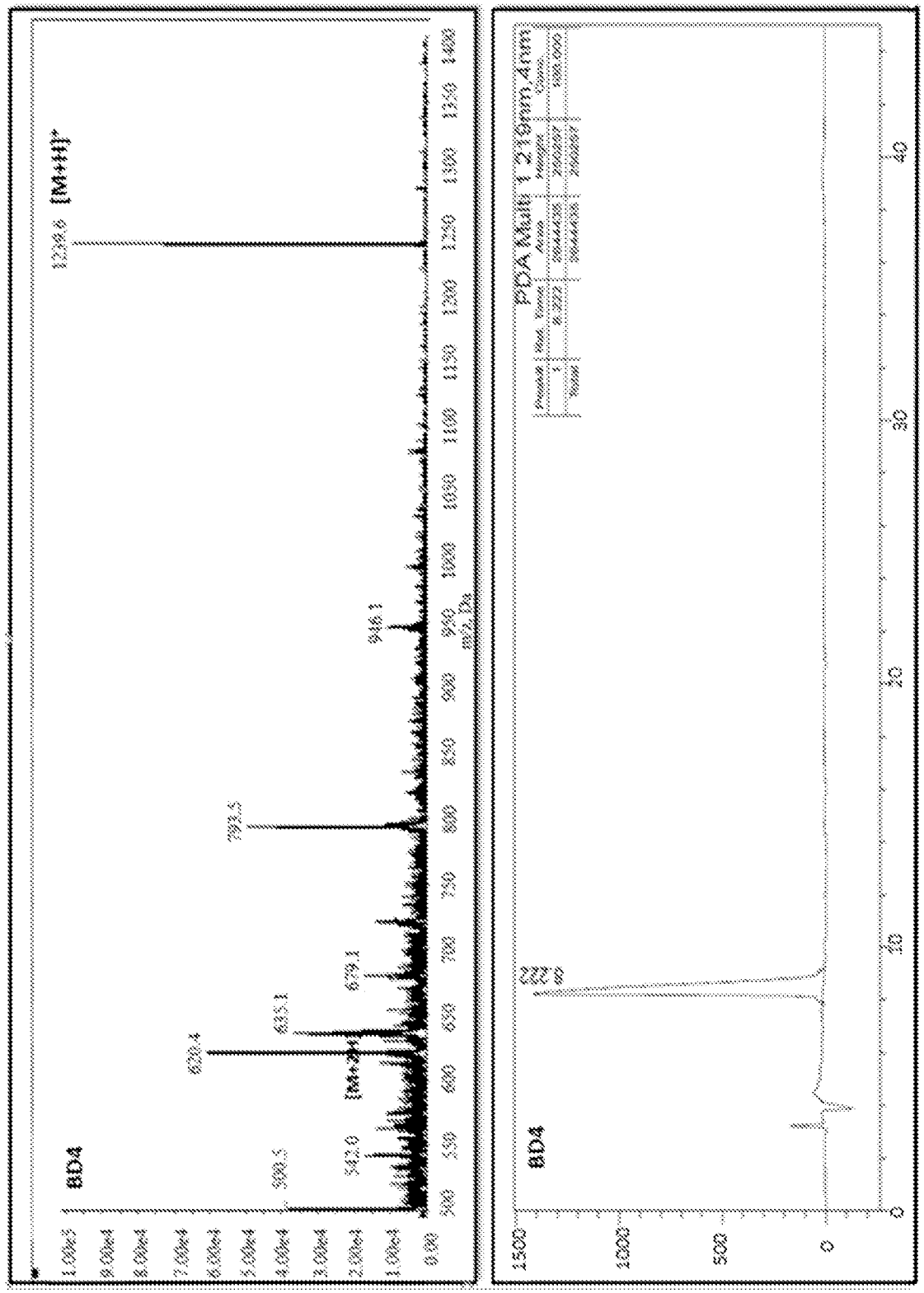
FIG. 16 shows mass spectrometry and HPLC traces for bioreducible dendrimer BD4.

Two classes of peptide dendrimer were designed and synthesized, by either installing the disulfide-bridged amino acid at the terminal head groups (BD1, BD2) or within the branching core (BD3, BD4). Furthermore, for each dendrimer class, both 4⁺ (BD1, BD3) and 8⁺ (BD2, BD4) systems were constructed. Fmoc-Cys(S—SC(CH₃)₂CH₂NH(Fmoc)-OH (compound 16) was trialled for the first time as a means of direct insertion of a biochemically stable disulfide via solid phase chemistry to both class of dendrimer. The general approach employed in synthesis of the dendrimers is shown schematically in FIG. 4. The disulfide-bridged amino acid was successfully installed in the branching core and separately, at the terminals of the dendrimer with a yield of ≥60% achieved. The yield and characterisation data of the synthesised dendrimers is shown in Table 2 while FIG. 13 is a representative RP-HPLC chromatogram of BD1.

Synthesis of 4⁺ Bioreducible Dendrimer ((SSa)₂-Lys-Gly, BD1)

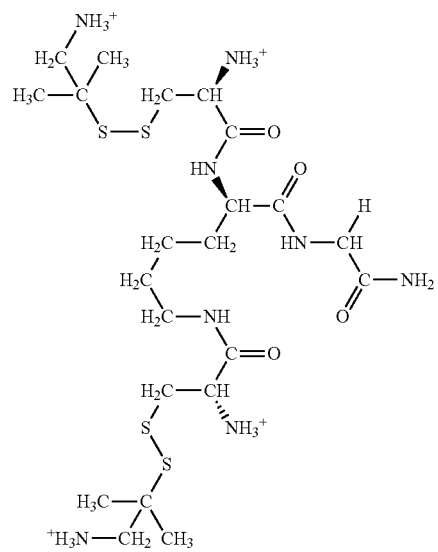 [SMILES: CC(C)(C[NH3+])SSC[C@@H]([NH3+])C(=O)NCCCC[C@@H](NC(=O)[C@H]([NH3+])CSSC(C)(C)C[NH3+])C(=O)NCC(N)=O]

Protocol for BD1 synthesis

The following steps are based on the general protocol described above:

1. Rink amide resin (0.2 g, loading capacity 0.79 mmol/g)
4. Fmoc-Gly-OH (0.140 g)
7. Repeated amino acid coupling with
   a. Fmoc-Lys(Fmoc)-OH (0.279 g)
   b. Fmoc-SSa(Fmoc)-OH (0.632 g, 6 eq).

After completion of coupling and deprotection reaction of a final amino acid of a sequence, steps 8-11 were performed to collect the final crude peptide. It will be understood by the person skilled in the art that the 4+ bioreducible dendrimer BD1 illustrated above will be isolated in the form of a TFA salt when cleavage from the resin is undertaken using the conditions given in step 9 above.

8+ Bioreducible Dendrimer ((SSa)$_4$-(Lys)$_2$-Lys-Gly, BD2)

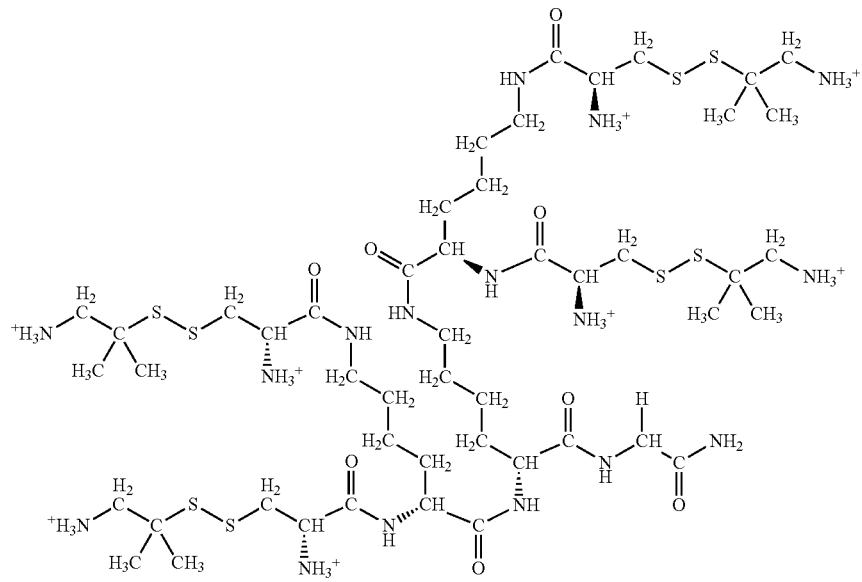 [SMILES: CC(C)(C[NH3+])SSC[C@@H]([NH3+])C(=O)NCCCC[C@@H](NC(=O)[C@H]([NH3+])CSSC(C)(C)C[NH3+])C(=O)NCCCC[C@@H](NC(=O)[C@@H](CCCCNC(=O)[C@H]([NH3+])CSSC(C)(C)C[NH3+])NC(=O)[C@H]([NH3+])CSSC(C)(C)C[NH3+])C(=O)NCC(N)=O]

Protocol for BD2 synthesis

The following steps are based on the general protocol described above:
1. Rink amide resin (0.2 g, loading capacity 0.34 mmol/g)
4. Fmoc-Gly-OH (0.060 g)
7. Repeated amino acid coupling with
   a. Fmoc-Lys(Fmoc)-OH (0.120 g)
   b. Fmoc-Lys(Fmoc)-OH (0.240 g; 6 eq)
   c. Fmoc-SSa(Fmoc)-OH (0.545 g; 12 eq).

After completion of coupling and deprotection reactions of the final amino acid of the sequence, steps 8-11 were performed to collect the final crude peptide. It will be understood by the person skilled in the art that the 8+ bioreducible dendrimer BD2 illustrated above will be isolated in the form of a TFA salt when cleavage from the resin is undertaken using the conditions given in step 9 above.

Synthesis of 4+ Bioreducible Dendrimer ((Arg)$_2$-SSa-Gly, BD3)

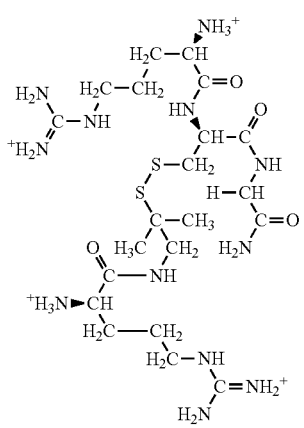 [SMILES: CC(C)(CNC(=O)[C@H]([NH3+])CCCNC(N)=[NH2+])SSC[C@@H](NC(=O)[C@H]([NH3+])CCCNC(N)=[NH2+])C(=O)NCC(N)=O]

Protocol for BD3 Synthesis

The following steps are based on the general protocol described above:

1. Rink amide resin (0.2 g, loading capacity 0.79 mmol/g)

4. Fmoc-Gly-OH (0.141 g; 3 eq w.r.t original resin loading)

7. Repeated amino acid coupling with a. Fmoc-SSa(Fmoc)-OH (0.316 g; 3 eq w.r.t original resin loading)

b. Fmoc-Arg(Pbf)-OH (0.64 g; 6 eq w.r.t original resin loading).

Please note that Pbf denotes a 2,2,4,6,7-pentamethyldihydrobenzofuran-5-sulfonyl protecting group After completion of coupling and deprotection reactions of the final amino acid of the sequence, steps 8-11 were performed to collect the final crude peptide. It will be understood by the person skilled in the art that the 4+ bioreducible dendrimer BD3 illustrated above will be isolated in the form of a TFA salt when cleavage from the resin is undertaken using the conditions given in step 9 above.

Synthesis of 8+ Bioreducible Dendrimer
((Arg)₄-(SSa)₂-Lys-Gly, BD4)

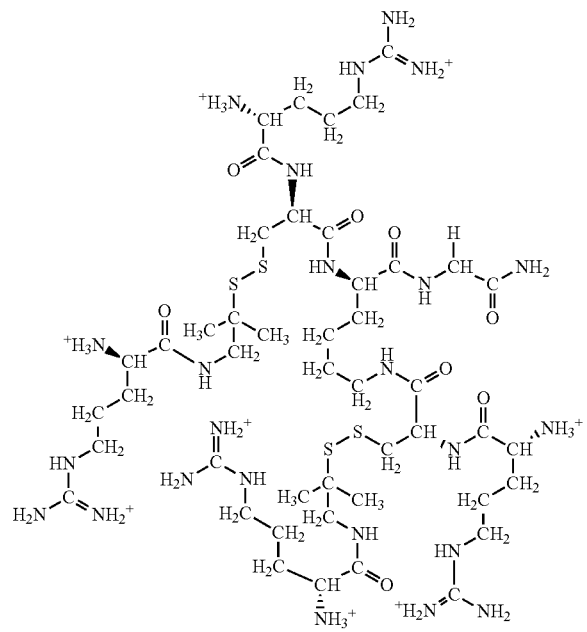 [SMILES: CC(C)(CNC(=O)[C@H]([NH3+])CCCNC(N)=[NH2+])SSC[C@@H](NC(=O)[C@H]([NH3+])CCCNC(N)=[NH2+])C(=O)NCCCC[C@@H](NC(=O)[C@@H](CSSC(C)(C)CNC(=O)[C@H]([NH3+])CCCNC(N)=[NH2+])NC(=O)[C@H]([NH3+])CCCNC(N)=[NH2+])C(=O)NCC(N)=O]

Protocol for BD4 Synthesis

The following steps are based on the general protocol described above:

1. Rink amide resin (0.2 g, loading capacity 0.34 mmol/g)
4. Fmoc-Gly-OH (0.60 g; 3 eq w.r.t original resin loading)
7. Repeated amino acid coupling with
   a. Fmoc-Lys(Fmoc)-OH (0.120 g; 3 eq w.r.t original resin loading)
   b. Fmoc-SSa(Fmoc)-OH (0.272 g; 6 eq w.r.t original resin loading)
   c. Fmoc-Arg(Pbf)-OH (0.528 g; 12 eq w.r.t original resin loading)

After completion of coupling and deprotection reaction of a final amino acid of a sequence, steps 8-11 were performed to collect the final crude peptide. It will be understood by the person skilled in the art that the 8+ bioreducible dendrimer BD4 illustrated above will be isolated in the form of a TFA salt when cleavage from the resin is undertaken using the conditions given in step 9 above.

Synthesis of Nonreducible Dendrimer
((Arg)₄-(Lys)₂-Lys-Gly, NRD)

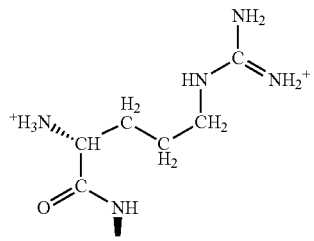

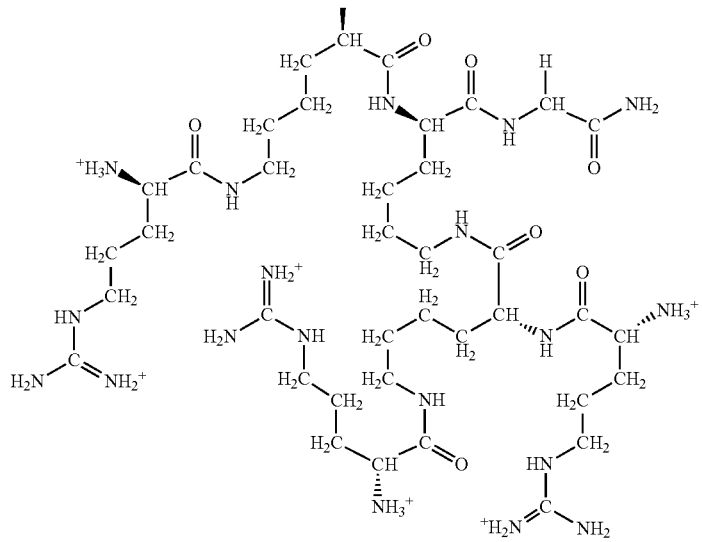

Protocol for NRD Synthesis

The following steps are based on the general protocol described above:
1. Rink amide resin (0.2 g, loading capacity 0.34 mmol/g)
4. Fmoc-Gly-OH (0.60 g; 3 eq w.r.t original resin loading)
7. Repeated amino acid coupling with
   a. Fmoc-Lys(Fmoc)-OH (0.120 g; 3 eq w.r.t original resin loading)
   b. Fmoc-Lys(Fmoc)-OH (0.226 g; 6 eq w.r.t original resin loading)
   c. Fmoc-Arg(Pbf)-OH (0.528 g; 12 eq w.r.t original resin loading)

After completion of coupling and deprotection reactions of the final amino acid of the sequence, steps 8-11 were performed to collect the final crude peptide. It will be understood by the person skilled in the art that the 8+ nonreducible dendrimer NRD illustrated above will be isolated in the form of a TFA salt when cleavage from the resin is undertaken using the conditions given in step 9 above.

Figure 17:
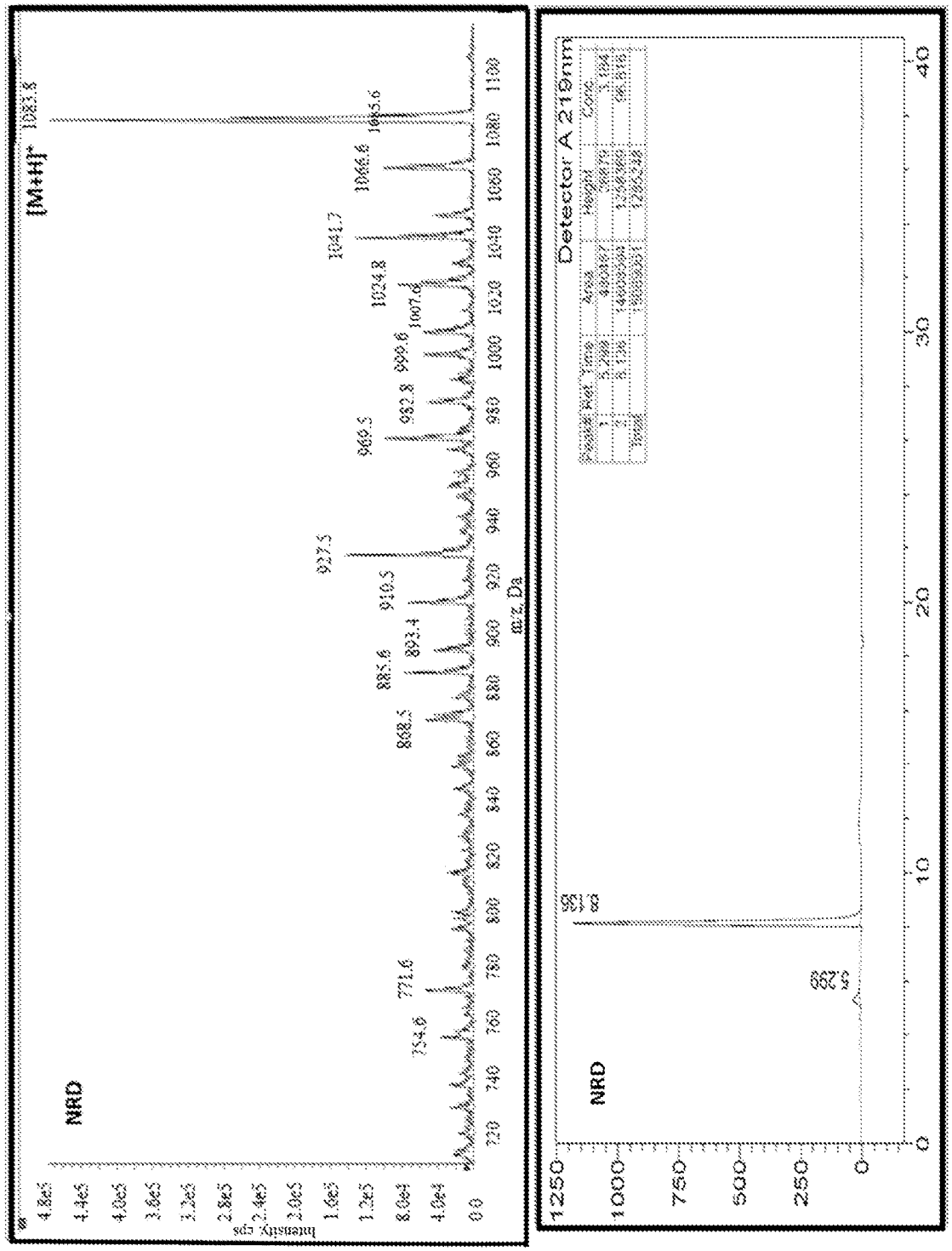
FIG. 17 shows mass spectrometry and HPLC traces for non-reducible dendrimer NRD.

Bioreducible dendrimers BD1-4 were successfully purified by preparative RP-HPLC and using ESI-MS, all dendrimers clearly showed the desired molecular ion $[M+H]^+$ which was in accordance with the theoretically calculated molecular weights of each dendrimer, thus confirming the formation of each target peptide dendrimer. The HPLC and mass spectrometry data for BD1-4 are shown in FIGS. 13 to 16 and those for NRD are seen in FIG. 17. All synthesized peptide dendrimers also exhibited single peak profiles in analytical RP-HPLC.

TABLE 2

ESI-MS (observed $[M + H]^+$) and RP-HPLC ($R_t$) data for bioreducible dendrimers

| Dendrimer | Yield (%) | Molecular formula | Calculated $[M + H]^+$ | Observed | $R_t$ (min) |
|---|---|---|---|---|---|
| BD1 | 62.45 | $C_{22}H_{46}N_8O_4S_4$ | 614.25 | 615.2 | 5.71 |
| BD2 | 58.00 | $C_{48}H_{97}N_{16}O_8S_8$ | 1282.55 | 1283.5 | 10.61 |
| BD3 | 60.11 | $C_{21}H_{44}N_{12}O_4S_2$ | 592.30 | 593.5 | 5.43 |
| BD4 | 55.65 | $C_{46}H_{94}N_{24}O_8S_4$ | 1238.65 | 1239.6 | 8.22 |
| NRD | 65.34 | $C_{45}H_{90}N_{24}O_8$ | 1082.74 | 1083.8 | 8.14 |

Reduction Properties of Disulfide Bridges in Peptide Dendrimers

Glutathione (GSH) is the predominant reducing agent present in concentrations ranging from 2-10 mM in the cytosol of human cells, with the range attributed to that found in different cell types, as well as healthy and diseased cells. The concentration of GSH in the extracellular environment however is comparatively lower, although extracellularly there also exist a variety of proteins, thiols and reducing enzymes which readily reduce native disulfide bridges into thiols. With current bioreducible carriers they have largely failed to withstand in vivo conditions leading to premature release of therapeutic cargo. The present compounds of the first aspect are engineered to acquire moderate stability such that it is able to withstand low (extracellular) concentrations of reducing agent (i.e. low μM) yet is efficiently cleaved at higher (i.e. low mM) concentrations found intracellularly.

Determination of DNA Complexation with Reduction Sensitive and Insensitive Dendrimers Under Simulated Extra- and Intracellular Conditions with GSH and DTT Bioreduction of the disulfide bond of the compounds of the first aspect in the dendrimers to simulated reductive conditions at 37° C. and also room temperature (RT) was assessed using GSH and also DTT as model reducing agents.

Initially, each dendrimer (Bioreducible BD4 and non-reducible —NRD) was mixed with DNA in ratios that yielded moderately positive zeta potential values, which was indicative of successful complexation. Zeta potential is a well known indicator of successful complexation (K. Luo, C. Li, L. Li, W. She, G. Wang, Z. Gu, *Arginine functionalized peptide dendrimers as potential gene delivery vehicles, Biomaterials*, 33 (2012) 4917-4927; K. Luo, C. Li, G. Wang, Y. Nie, B. He, Y. Wu, Z. Gu, *Peptide dendrimers as efficient and biocompatible gene delivery vectors: synthesis and in vitro characterization, Journal of controlled release*, 155 (2011) 77-87).

DNA complexation was carried out by preparing BD4 (8+ non-reducible dendrimer (($Arg)_4$-$(Lys)_2$-Lys-Gly)), 100 μg/mL, in 7.4 pH phosphate (20 mM) buffer. To 10 μL of this solution was added 10 μL of circular DNA, being the CYP82E (cDNA) gene originating from the *Nicotiana* plant species, (40 nM 0.5 Kbp). The mixture was vortexed for 5 s and incubated for 45 min to 1 h to facilitate complex formation. Zeta potential measurements of BD4 dendrimer and DNA alone and the dendrimer:DNA complexes was determined using a Nano ZS (Malvern Instruments Limited, UK). Despite DNA possessing a considerable 'negative' zeta potential, mixing with the cationic dendrimer (BD4) resulted in an overall positive zeta potential, evidence of complexation occurring between the two oppositely charged species (Table 3).

TABLE 3

Zeta potential measurements of BD4 (in triplicate) and DNA (in triplicate) alone, followed by zeta potential measurements of their complex.

| BD4 (100 μg/mL) | DNA (40 nM) | BD4: DNA complexes |
|---|---|---|
| +8.16 | −18.76 | +4.32 |
| +7.51 | −17.90 | +4.19 |
| +7.89 | −18.01 | +4.18 |

The basis of zeta-potential measurements lie around the fact that genetic material is negatively charged, while the dendrimers are basic and so positively charged. This complementarity is what initiates complexation. In order for complete complexation and condensation of the genetic material to have occurred it is necessary to neutralise all the negative charge on the genetic material, and to drive this to a mildly positive zeta potential. This is also key in order to drive interaction of the resultant polyplex with the cell membrane of mammalian cells which are covered in carbohydrates and so possess a net negative surface charge.

Next, two dendrimers were selected for the bioreduction assay. BD4 and NRD (8+ non-reducible dendrimer (($Arg)_4$-$(Lys)_2$-Lys-Gly)), 1 mg/mL, were prepared in 7.4 pH phosphate (20 mM) buffer and incubated with different concentrations of GSH or DTT (dithiothreitol) ranging from 0.1 to 100 mM at room temperature and 37° C. overnight (12 h), followed by addition of 10 μL of circular DNA, being the CYP82E (cDNA) gene originating from the *Nicotiana* plant species, (40 nM 0.5 Kbp) (ratios were chosen based on zeta potentials of the dendrimer: DNA complex). The mixture was vortexed for 5 s and incubated for 45 min to 1 h to facilitate complex formation. Each dendrimer alone i.e. BD4 and NRD in the absence of either reducing agent incubated at 37° C. and RT, was used as a positive control and prepared at similar concentrations to form DNA complexes. A free DNA sample was used as a negative control.

Gel Electrophoresis

Figure 7:
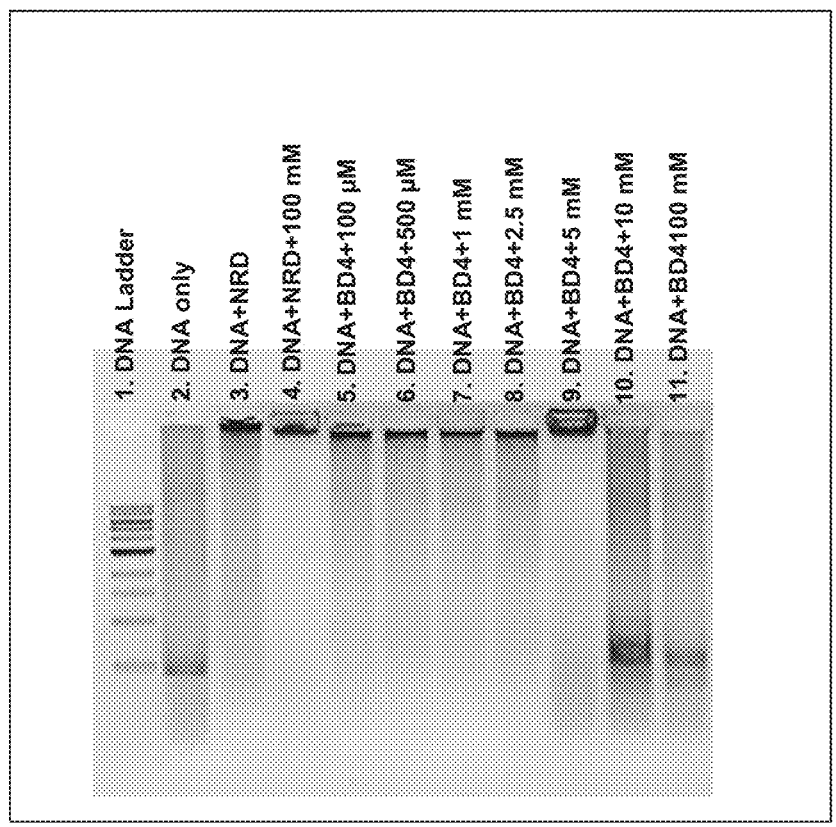
FIG. 7 is an image of DNA migration profiles using gel electrophoresis following incubation of dendrimer (non-reducible and bioreducible) with GSH at 37° C.

A 10 μL aliquot of each peptide dendrimer-DNA complex mixture was mixed with 3 μL of loading gel and all samples were then loaded on a 1% agarose gel containing 0.5 μg/mL ethidium bromide. Electrophoresis was performed at 90 V for 30 min, after which images of the gel were taken under UV-illumination and observed for DNA migration. The gel image is shown in FIG. 7.

Dendrimers incubated with increasing concentrations of GSH (and DTT) i.e. 100 μM to 100 mM at both RT and 37° C. showed interesting trends that evidence the stability of the present S—S-linker to reductive conditions reflective of the extracellular environment. Temperature of incubation with reducing agent played an important role in reduction of the S—S-linkages and so the carrier system, leading to the release and migration of DNA across the gel only when incubated at body temperature (FIG. 7, lanes 10 & 11). At room temperature disulfide bridges were stable even in the presence of 10 mM GSH (and DTT) reducing only with 100 mM of either reducing agent, whereas at 37° C. cleavage of disulfides and release of DNA occurred at 10 mM GSH (or DTT).

Results

Design and Development of a Bioreducible FRET Probe-Based System

In-Solution Chemical Synthesis of FRET Probe

Figure 8:
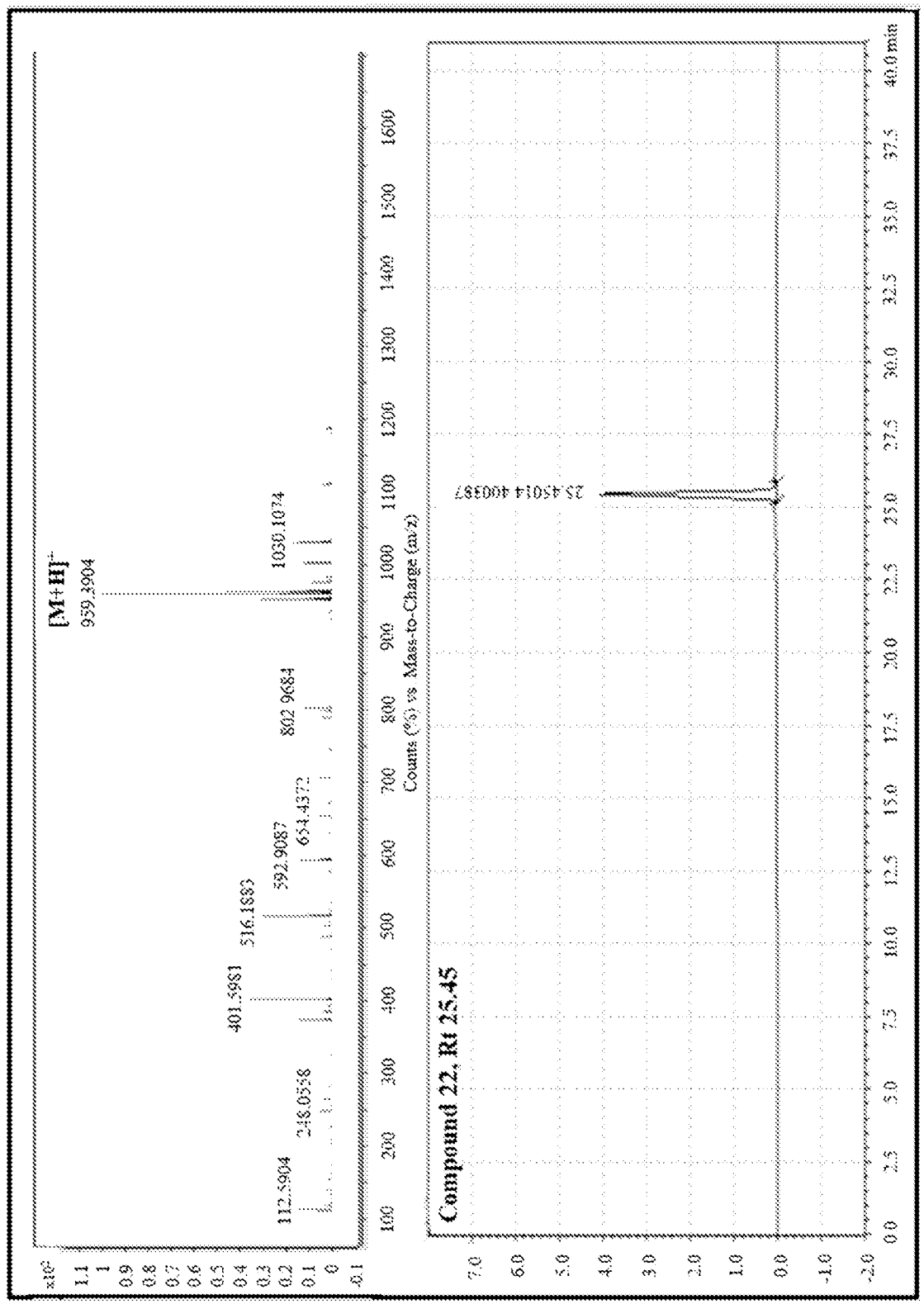
FIG. 8 is an HR-MS identifying a synthesised FRET probe.
Figure 9:
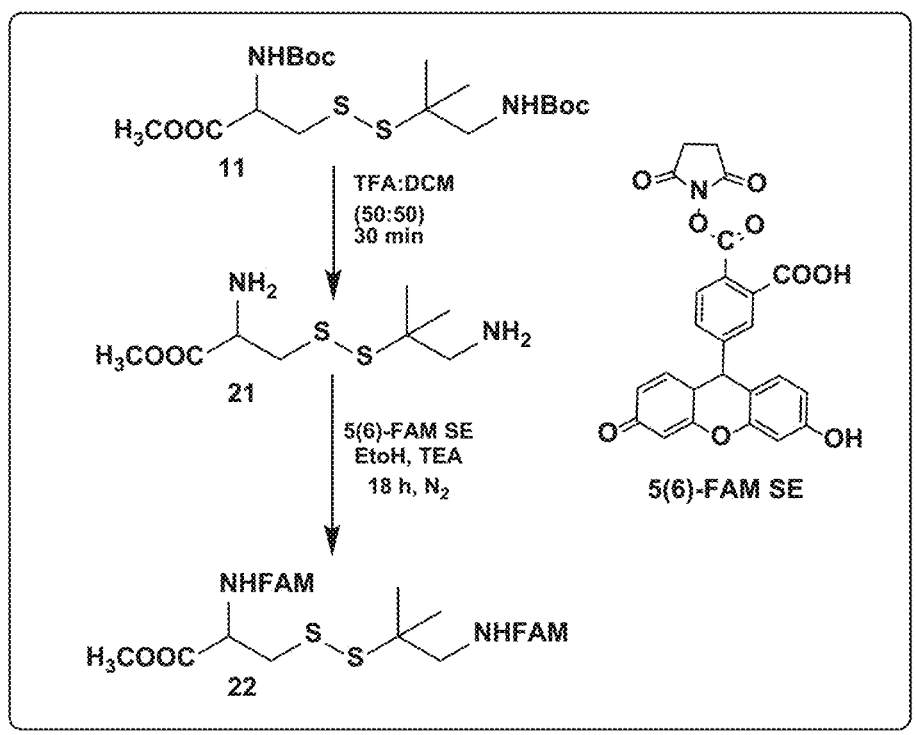
FIG. 9 is a synthetic scheme showing formation of a disulfide bond containing amino acid of the first aspect coupled with a FRET probe.

A solution of Boc-Cys(S—SC(CH$_3$)$_2$CH$_2$NH(Boc))—OCH$_3$ (5 μmol, 2.25 mg) in CH$_2$Cl$_2$ (1 mL) with TFA (1 mL) was stirred for 30 min at RT, for simultaneous removal of Boc-protecting groups, after which the solvents were removed in vacuo. Without further purification, 5(6)-carboxyfluorescein N-hydroxysuccinimide ester (10 μmol, 4.73 mg) in ethanol (1 mL) and TEA (100 μL) was added to the mixture, which was stirred for 18 h at RT under an inert (N$_2$) atmosphere. Solvent was then removed in vacuo and the product (compound 22) was obtained by preparative HPLC. The probe was characterised by HR-MS, and the molecular ion was detected as shown in the spectra seen in FIG. 8 HR-MS [M+H]$^+$ calculated for C$_{50}$H$_{43}$N$_2$O$_{14}$S$_2$$^+$, 959.2156; found, 959.3904. Yield (15%, 1.4 mg). The synthetic approach is shown in FIG. 9.

Dequenching Assay in Presence of DTT

A stock solution of a compound of the first aspect (compound 22) coupled to FRET (referred to herein as SS-FRET probe) (100 μM) was prepared in DMSO and then serial diluted to 0.1 μM with phosphate buffer (20 mM, pH 7.4). Similarly, a 100 mM stock solution of DTT was prepared and serial diluted to 100 μM. For each concentration of SS-FRET and DTT, a 10 μL sample of the SS-FRET solution was mixed with a 90 μL aliquot of DTT solution in a well of a black microtiter plate, and the fluorescence intensity of each well was recorded at 5 min intervals for 2 h at 37° C. using a fluorescence plate reader (FLUOstar Omega). Each experiment was performed in triplicate, with the average of the three readings being used in all subsequent analyses. Phosphate buffer was used as a control for both the SS-FRET probe and DTT.

Figure 10:
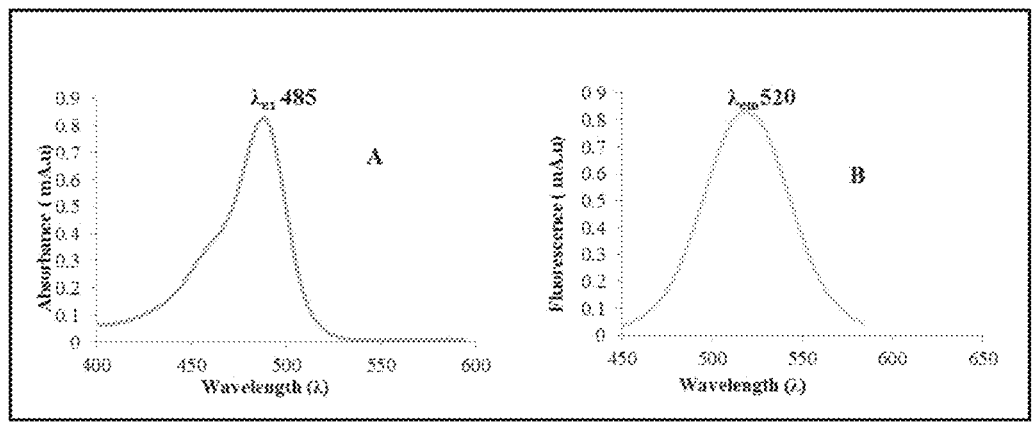
FIG. 10 is A) an excitation spectra ($\lambda_{ex}$ 485 nm), and B) an emission spectra ($\lambda_{em}$ 520, presence of 100 mM DTT) of a disulfide-bridged FRET probe.
Figure 11:
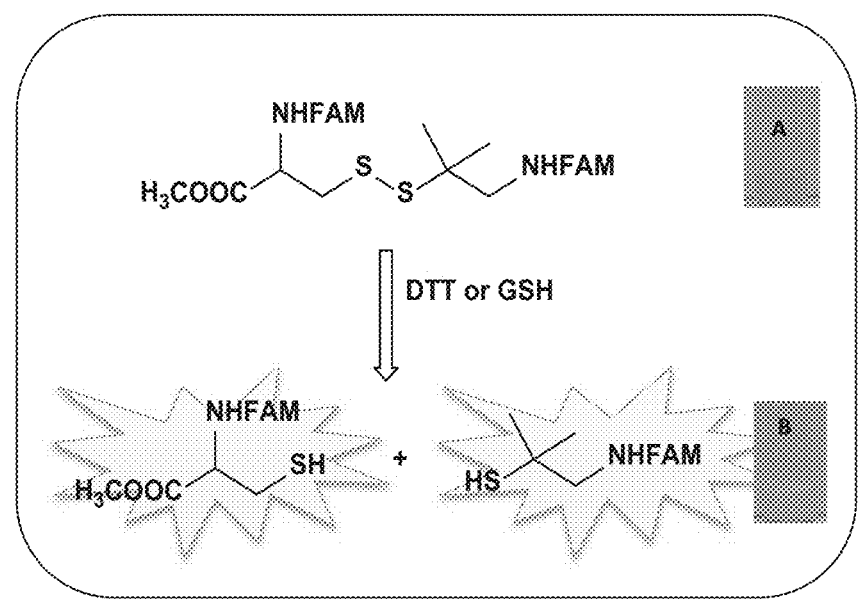
FIG. 11 is a scheme showing the reduction of a disulfide-bridged FRET probe in the presence of DTT.

Initially, as shown in FIG. 10, excitation ($\lambda_{ex}$) and emission spectra ($\lambda_{em}$) were obtained by addition of 100 mM of DTT to the SS-FRET synthesised above. FIG. 11 is a scheme for reduction of a disulfide-bridged FRET probe in the presence of DTT wherein, in the reaction vial, a yellow colour indicates a disulfide-bridged FRET probe solution and emission of green fluorescence indicates reduction of the disulfide bond of the FRET probe in the presence of 100 mM DTT.

Figure 12:
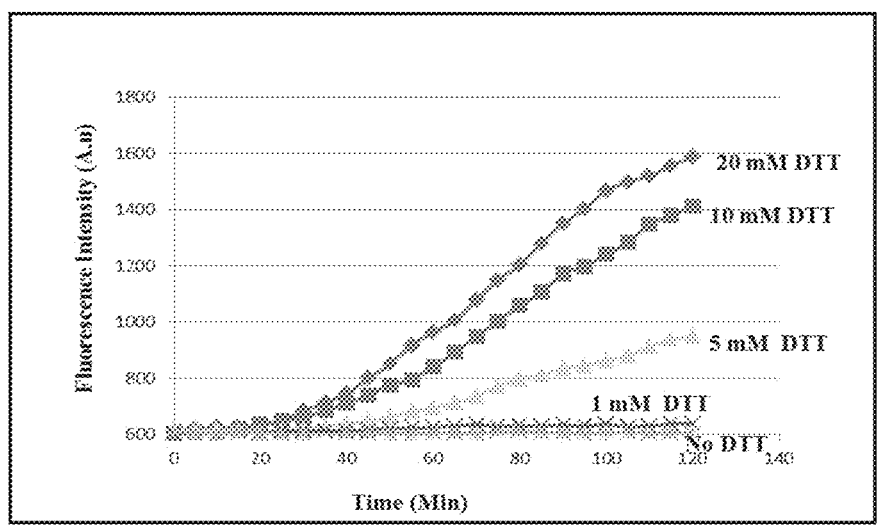
FIG. 12 is a graphical representation of the results of SS-FRET probe reduction experiments under different concentrations of DTT at 37° C.

The reduction behaviour of the SS-FRET synthesised above was then measured in the presence of 1 mM to 20 mM DTT. A hindered disulfide bond, such as is provided by compounds of the first aspect, was found to be stable to low concentrations of DTT. In this experiment, the disulfide bridged FRET probe was incubated with 1, 5, 10 and 20 mM DTT and the extent of reduction achieved was monitored by observing the corresponding fluorescence seen with reduction. No change in fluorescence was observed for the probe in the presence of 0 and 1 mM of DTT, whereas in the presence of 5 mM DTT a partial increase in the fluorescence was observed. The fluorescence in the presence of 10 and 20 mM showed a significant increase which indicates substantial reduction of the SS-FRET probe. The results are shown graphically in FIG. 12 where the increase in fluorescence can be seen with increasing DTT exposure concentrations. These results indicate that disulfide-bridges formed using the compounds of the first aspect are stable to low concentrations of reducing agents i.e., DTT (=GSH), but they preferentially reduce under high concentrations at ≥5 mM of DTT. These results were in line with the reduction of disulfide bridges in bioreducible dendrimers discussed earlier.

All references, including publications, patent applications, and patents, cited herein are incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Unless defined otherwise, all technical and scientific terms used herein have the same meaning as would be commonly understood by those of ordinary skill in the art to which this invention belongs.

The invention claimed is:

1. A compound of formula XI, or a salt thereof:

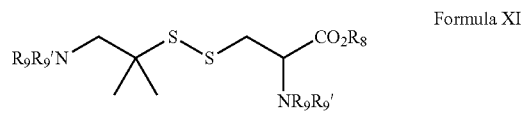

Formula XI wherein R$_8$ is selected from the group consisting of hydrogen, a counterion, and a carboxylic acid protecting group, wherein the carboxylic acid protecting group is selected from the group consisting of:
C$_1$-C$_6$ alkyl, wherein the C$_1$-C$_6$ alkyl is optionally substituted by one or more groups selected from: halo and alkoxy;
benzyl, wherein the benzyl is optionally substituted by one or more groups selected from: alkyl, cycloalkyl, halo, hydroxyl, alkoxy and nitro;
phenyl which is 2,6-disubstituted by one or more groups selected from: alkyl, cycloalkyl, halo, hydroxyl, alkoxy and nitro;
silyl, substituted by one or more groups selected from: alkyl and aryl; and
oxazolyl; and wherein:
  each $R_9$ is independently selected from the group consisting of fluorenylmethoxycarbonyl (Fmoc), t-butyloxycarbonyl (Boc), benzyloxycarbonyl (carboxybenzyl, Cbz), p-methoxybenzyloxycarbonyl (Moz, MeOZ), formyl, acetyl (Ac), trifluoroacetyl, trichloroacetyl, benzoyl (Bz), p-methoxyphenyl (PMP), benzyl (Bn), p-methoxybenzyl (PMB), 3,4-dimethoxybenzyl (DMPM), 2,4-dimethoxybenzyl (Dmb), triphenylmethyl (trityl, Tr), 4-methyltriphenylmethyl (4-methyltrityl, Mtt), 4-methoxytriphenylmethyl (4-methoxytrityl, Mmt), diphenylmethylene, N-1-(4,4-dimethyl-2,6-dioxocyclohexylidene)ethyl (Dde), benzene sulfonyl, p-toluenesulfonyl (tosyl), and 2,2,4,6,7-pentamethyldihydrobenzofuran-5-sulfonyl (Pbf), and
  each $R_9'$ is hydrogen.

2. The compound according to claim 1, wherein $R_8$ is hydrogen, or $R_8$ is a $C_1$-$C_6$ alkyl.

3. The compound according to claim 1, wherein $R_8$ is selected from the group consisting of hydrogen, $C_1$-$C_6$ alkyl, trihalo$C_1$-$C_6$alkyl, trialkoxy$C_1$-$C_6$alkyl, benzyl, nitrobenzyl, 2,6-dimethylphenyl, 2,6-diisopropylphenyl, 2,6-di-t-butylphenyl, trialkylsilyl and oxazolyl.

4. The compound of claim 1, which is:

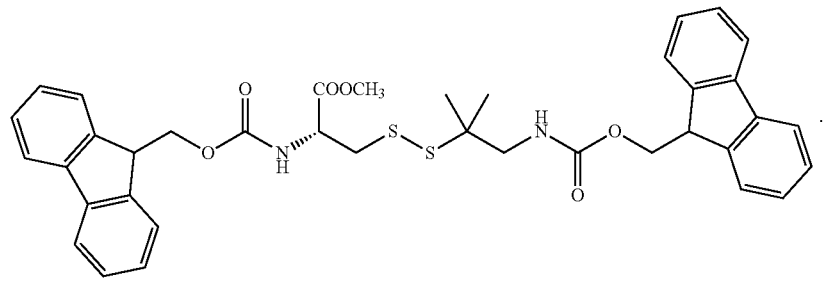 [SMILES: COC(=O)[C@H](CSSC(C)(C)CNC(=O)OCC1c2ccccc2-c2ccccc21)NC(=O)OCC1c2ccccc2-c2ccccc21]

5. The compound of claim 1, which is:

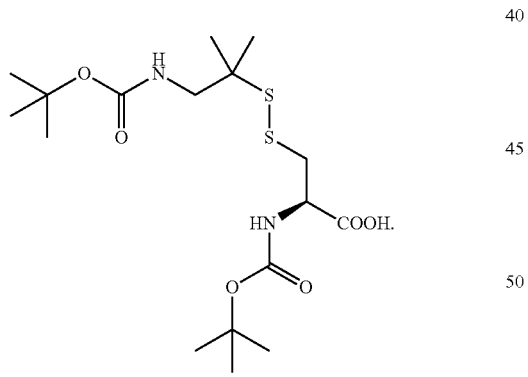

6. The compound of claim 1, which is:

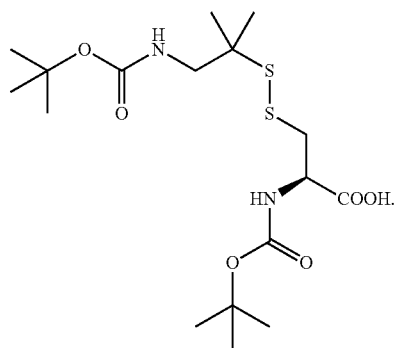 [SMILES: CC(C)(C)OC(=O)NCC(C)(C)SSC[C@H](NC(=O)OC(C)(C)C)C(=O)O]

7. The compound of claim 1, which is:

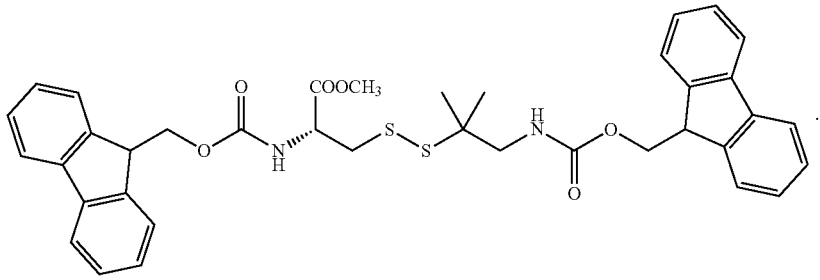 [SMILES: COC(=O)[C@H](CSSC(C)(C)CNC(=O)OCC1c2ccccc2-c2ccccc21)NC(=O)OCC1c2ccccc2-c2ccccc21]

8. The compound of claim 1, which is:
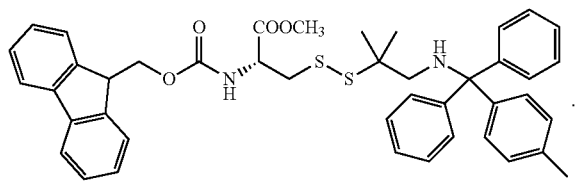 [SMILES: COC(=O)[C@H](CSSC(C)(C)CNC(c1ccccc1)(c1ccccc1)c1ccc(C)cc1)NC(=O)OCC1c2ccccc2-c2ccccc21]
9. The compound of claim 1, which is:
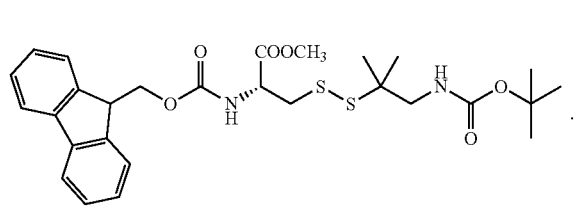 [SMILES: COC(=O)[C@H](CSSC(C)(C)CNC(=O)OC(C)(C)C)NC(=O)OCC1c2ccccc2-c2ccccc21]
10. The compound of claim 1, which is:
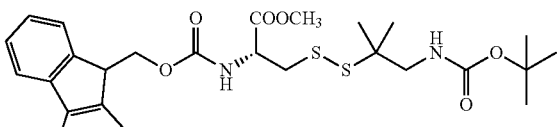
11. The compound of claim 1, which is:
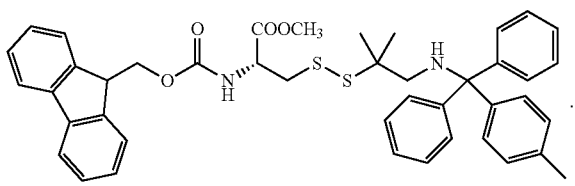 [SMILES: COC(=O)[C@H](CSSC(C)(C)CNC(c1ccccc1)(c1ccccc1)c1ccc(C)cc1)NC(=O)OCC1c2ccccc2-c2ccccc21]
\* \* \* \* \*